(12) United States Patent
Tadipartiii et al.

(10) Patent No.: US 7,759,350 B2
(45) Date of Patent: Jul. 20, 2010

(54) PYRIMIDINE CARBOXAMIDES

(75) Inventors: Ravikumar Tadipartiii, Tamil Nadu (IN); Venkatesan Parameswaran, Tamil Nadu (IN); Rajib Barik, Tamil Nadu (IN); Gaddam Om Reddy, Tamil Nadu (IN); Pawan Aggarwal, Tamil Nadu (IN); Sappanimuthu Thirunavukkarasu, Tamil Nadu (IN); Sriram Rajagopal, Tamil Nadu (IN)

(73) Assignee: Orchid Research Laboratories Ltd., Chennai (IN)

( * ) Notice: Subject to any disclaimer, the term of this patent is extended or adjusted under 35 U.S.C. 154(b) by 912 days.

(21) Appl. No.: 11/516,549

(22) Filed: Sep. 7, 2006

(65) Prior Publication Data

US 2007/0072876 A1   Mar. 29, 2007

(30) Foreign Application Priority Data

Sep. 15, 2005   (IN) ...................... 1302/CHE/2005

(51) Int. Cl.
  *C07D 239/28* (2006.01)
  *A61K 31/505* (2006.01)
(52) U.S. Cl. .................. 514/252.14; 514/256; 514/269; 544/295; 544/319; 544/328
(58) Field of Classification Search ................. 544/295, 544/319, 328; 514/252.14, 256, 269
  See application file for complete search history.

(56) References Cited

FOREIGN PATENT DOCUMENTS

| EP | 1223170 | | 7/2002 |
|---|---|---|---|
| GB | 2406856 | * | 4/2005 |
| JP | 2000-226372 | | 8/2000 |
| WO | WO 95/25723 | | 9/1995 |
| WO | WO 2005/032493 | | 4/2005 |
| WO | WO 2007/041634 | * | 4/2007 |

OTHER PUBLICATIONS

Ulrich, Chapter 4: Crystallization, Kirk-Othmer Encyclopedia of Chemical Technology, Aug. 2002.*
Simone, Oncology: Introduction, Cecil Textbook of Medicine, 20th Edition, vol. 1, pp. 1004-1010, 1996.*
Casanova et al., PubMed Abstract (Rev Neurol. 28(9):909-15) May 1999.*
Freston, PubMed Abstract (Am J Med 107(6A):78S-88S; discussions) Dec. 1999.*
Naesdal et al., PubMed Abstract (Eur J Gastroenterol Hepatol. 13(12):1401-6) Dec. 2001.*
Vippagunta et al., Cyrstalline Solids, Advanced Drug Delivery Reviews, 48, pp. 3-26, 2001.*
West, Solid Solutions, Solid State Chemistry and its applications, pp. 358 & 365, 1988.*
Schwink et al., CAPLUS Abstract 141:225302 (2004).*
Sekiguchi et al., CAPLUS Abstract 138:321285 (2003).*
Palanki et al., CAPLUS Abstract 133:358879 (2000).*
Miyahara et al., CAPLUS Abstract 133:135326 (2000).*
Katsuhira et al., CAPLUS Abstract 132:78562 (2000).*
Akiyama et al., CAPLUS Abstract 131:199705 (1999).*
Riordan et al., CAPLUS Abstract 124:117098 (1995).*
El-Kerdawy et al., CAPLUS Abstract 114:101905 (1991).*
Kim, CAPLUS Abstract 103:87832 (1985).*
Machon et al., CAPLUS Abstract 102:45867 (1985).*
Kampe, CAPLUS Abstract 97:109955 (1982).*
Moorthy S. S. Palanki et al., "Inhibitors of NF-kB and AP-1 Gene Expression: SAR Studies on the Pyrimidine Portion of 2-Chloro-4-trifluoromethylpyrimidine-5-[N-(3',5'-bis(trifluoromethyl)phenyl)carboxamide]", Journal of Medicinal Chemistry (2000), 43(21), pp. 3995-4004.
Klaus Dieter Kampe, "2-Cyano-3-ethoxyacrylamides—Selective Synthons for the Synthesis of Heterocycles", Angewandte Chemie (1982), 94(7), pp. 540-541.

* cited by examiner

*Primary Examiner*—Deepak Rao
(74) *Attorney, Agent, or Firm*—Oliff & Berridge, PLC

(57) ABSTRACT

The present invention relates to novel compounds of the general formula (I), their derivatives, their analogs, their tautomeric forms, their stereoisomers, their polymorphs, their hydrates, their solvates, their pharmaceutically acceptable salts and compositions, their metabolites and prodrugs thereof. The present invention more particularly relates to novel pyrimidine carboxamides of the general formula (I). Also included is a method of prophylaxis or treatment of a pain disorder, immunological diseases, inflammation, rheumatoid arthritis; osteoporosis; multiple myeloma; uveititis; acute and chronic myelogenous leukemia; ischemic heart disease; atherosclerosis; cancer; ischemic-induced cell damage; pancreatic beta cell destruction; osteoarthritis; rheumatoid spondylitis; gouty arthritis; inflammatory bowel disease; adult respiratory distress syndrome (ARDS); psoriasis; Crohn's disease; allergic rhinitis; ulcerative colitis; anaphylaxis; contact dermatitis; muscle degeneration; cachexia; asthma; bone resorption diseases; ischemia reperfusion injury; brain trauma; multiple sclerosis; sepsis; septic shock; toxic shock syndrome; fever, and myalgias due to infection in a mammal comprising administering an effective amount of a compound of formula (I) as described above.

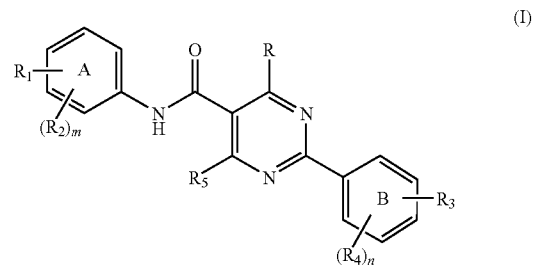

(I)

11 Claims, No Drawings

PYRIMIDINE CARBOXAMIDES

FIELD OF THE INVENTION

The present invention relates to novel compounds of the general formula (I), their derivatives, their analogs, their tautomeric forms, their stereoisomers, their polymorphs, their hydrates, their solvates, their pharmaceutically acceptable salts and compositions, their metabolites and prodrugs thereof. The present invention more particularly relates to novel pyrimidine carboxamides of the general formula (I).

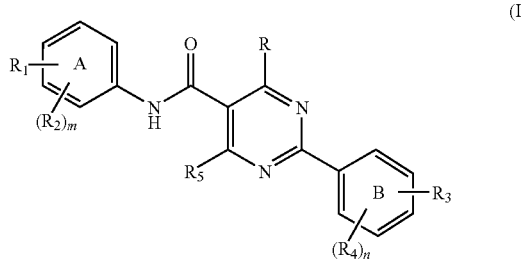

The present invention also provides a process for the preparation of the above said novel compounds of the formula (I), their derivatives, analogs, tautomeric forms, stereoisomers, polymorphs, hydrates, solvates, pharmaceutically acceptable salts and compositions, metabolites and prodrugs thereof. This invention also relates to intermediates useful in the preparation of such compounds.

The novel compounds of the present invention are useful for the treatment of inflammation and immunological diseases; particularly those mediated by cytokines such as TNF-α, IL-1, IL-6, IL-1β, IL-8, IL-12 and cyclooxygenases such as COX-2 and COX-3 and diseases mediated by thromboxane synthase.

The compounds of the present invention are also useful for the treatment of rheumatoid arthritis; osteoporosis; multiple myeloma; uveititis; acute and chronic myelogenous leukemia; ischemic heart disease; atherosclerosis; cancer; ischemic-induced cell damage; pancreatic β cell destruction; osteoarthritis; rheumatoid spondylitis; gouty arthritis; inflammatory bowel disease; adult respiratory distress syndrome (ARDS); psoriasis; Crohn's disease; allergic rhinitis; ulcerative colitis; anaphylaxis; contact dermatitis; asthma; muscle degeneration; cachexia; type I and type II diabetes; bone resorption diseases; ischemia reperfusion injury; brain trauma; multiple sclerosis; sepsis; septic shock; toxic shock syndrome; fever, and myalgias due to infection.

BACKGROUND OF INVENTION

Signals necessary for cell growth, differentiation, response to bioregulatory molecules, infectious agents and physiological stress involve changes in the rates of gene expression. The ability to respond appropriately to such signaling events challenges the survival of the cell and ultimately the organism. Pertrubations in the normal regulation of these specific genetic responses can result in pathogenic events that lead to acute and chronic diseases. In certain autoimmune diseases or chronic inflammatory states, continuous activation of T-cells eventually leads to a self-perpetuating destruction of normal tissues or organs. This caused by the induction of adhesion molecules, chemotaxis of leukocytes, activation of leukocytes and the production of mediators of inflammation, all of these events are regulated at the level of transcription for the production of new proteins, including cytokines. The production of cytokines, as well as a number of other cellular regulators, is controlled by a family of proteins, known as transcription factors (TFs). These transcription factors, when activated, bind to specific regions on the DNA and act as molecular switches or messengers to induce or upregulate gene expression. The activation of these TFs is caused by a variety of external signals including physiological stress, infectious agents and other bioregulatory molecules. Once the plasma membrane receptors are activated, a cascade of protein kinases and second messengers are induced which, in turn, result in the production of RNA transcripts. The end result is the production of RNA transcripts, and proinflammatory proteins via translation and processing of the RNA transcripts.

The activation system can, at times, be very robust. For example, a specific set of external signals could result in a single transcription factor to induce many proteins responsible for a given disease. Therefore, regulating this process by disrupting the production of activated TF(s) has the potential to attenuate the production of the associated pathological proteins, thereby halting or reversing the course of the disease.

Two transcription factors, NFkB and AP-1, have been show to regulate the production of many proinflammatory cytokines and related proteins that are elevated in immunoinflammatory diseases. These TFs regulate interleukin-1 (IL-1), interleukin-2 (IL-2), tumor necrosis factor-α (TNF-α), interleukin-6 (IL-6) and interleukin-8 (IL-8) levels in a variety of cell types. For example, NFkB and other related complexes are involved in the rapid induction of genes whose products function in the protective and proliferative responses upon exposure of cells to external stimuli. Similarly, AP-1 has a significant role in the regulation of IL-2 and TNF-α transcription during T-cell activation. In addition, TNF-α and IL-1 are strong activators of collagenase, gelatinase and stromelysin gene expression, which require a single AP-1 binding site in the promoter region of these genes. Therefore, an inhibitor of NFkB and/or AP-1 activation would coordinately repress the activities of a series of proteinases. In addition, cell adhesion molecules are also controlled by these TFs. All of these proteins have shown to play a role in diseases, including osteoarthritis, transplant rejection, ischemia, reperfusion injury, trauma, certain cancers, viral disorders, and autoimmune diseases such a rheumatoid arthritis, multiple sclerosis, psoriasis, inflammatory bowel disease, glomerulonephritis, lupus and juvenile diabetes, In summary, the role of these TFs is to act as a transducer for certain stimuli that lead to immune, inflammatory, and acute phase responses.

Since many diseases are caused by the inappropriate production of proteins, conventional therapeutic approaches have focused on inhibiting function or activity of individual effector proteins. These treatments have not always proved to be effective and, at times, are associated with many undesirable side effects. Therefore, there is a need for new therapies for the prevention and/or treatment of immunoinflammatory and autoimmune diseases. More specifically, there is a need for compounds that prevent, preferably by inhibiting transcription at an early stage, the production of proteins associated with immunoinflammatory and autoimmune diseases. Furthermore, these compounds should inhibit the kinase(s) that regulate the activation of TFs such as NFkB and AP-1. The present invention fulfills these needs and provides further related advantages.

The present invention is concerned with the treatment of immunological diseases or inflammation, notably such diseases are mediated by cytokines or cyclooxygenases. The principal elements of the immune system are macrophages or antigen-presenting cells, T cells and B cells. The role of other immune cells such as NK cells, basophils, mast cells and dendritic cells are known, but their role in primary immunologic disorders is uncertain. Macrophages are important mediators of both inflammation and provide the necessary "help" for T cell stimulation and proliferation. Most importantly macrophages make IL-1, IL-12 and TNF-α all of which are potent pro-inflammatory molecules and also provide help for T cells. In addition, activation of macrophages results in the induction of enzymes, such as cyclooxygenase-2 (COX-2) and cyclooxygenase-3 (COX-3), inducible nitric oxide synthase (iNOS) and production of free radicals capable of damaging normal cells. Many factors activate macrophages, including bacterial products, superantigens and interferon gamma (IFNγ). It is believed that phosphotyrosine kinases (PTKs) and other undefined cellular kinases are involved in the activation process.

Cytokines are molecules secreted by the immune cells and large numbers of chronic and acute conditions have been recognized to be associated with perturbation of the inflammatory response. A large number of cytokines participate in this response, including IL-1, IL-6, IL-8 and TNF. It appears that the activity of these cytokines in the regulation of inflammation rely at least in part on the activation of an enzyme on the cell signalling pathway, a member of the MAP known as CSBP and RK. This kinase is activated by dual phosphorylation after stimulation by physiochemical stress, treatment with lipopolysaccharides or with proinflammatory cytokines such as IL-1 and TNF. Therefore, inhibitors of the kinase activity of p38 are useful anti-inflammatory agents.

Cytokines are molecules secreted by the immune cells that are important in mediating immune responses. Cytokine production may lead to the secretion of other cytokines, altered cellular function, cell division or differentiation. Inflammation is the body's normal response to injury or infection. However, in inflammatory diseases such as rheumatoid arthritis, pathologic inflammatory processes can lead to morbidity and mortality. The cytokine, TNF-α, plays a central role in the inflammatory response and has been targeted as a point of intervention in inflammatory diseases. TNF-α is a polypeptide hormone released by activated macrophages and other cells. At low concentrations, TNF-α participates in the protective inflammatory response by activating leukocytes and promoting their migration to the extravascular sites of inflammation (Moser et al., J Clin Invest, 83, 444-55, 1989). At higher concentrations, TNF-α can act as a potent pyrogen and induce the production of other pro-inflammatory cytokines (Haworth et al., Eur J Immunol, 21, 2575-79, 1991; Brennan et al., Lancet, 2, 244-7, 1989). TNF-α also stimulates the synthesis of acute-phase proteins. In rheumatoid arthritis, a chronic and progressive inflammatory disease affecting about 1% of the adult U.S. population, TNF-α mediates the cytokine cascade that leads to joint damage and destruction (Arend et al., Arthritis Rheum, 38, 151-60, 1995). Inhibitors of TNF-α, including soluble TNF receptors (etanercept) (Goldenberg, Clin Ther, 21, 75-87, 1999) and anti-TNF-α antibody (infliximab) (Luong et al., Ann Pharmacother, 34, 743-60, 2000), have been recently approved by the U.S.FDA as agents for the treatment of rheumatoid arthritis.

Elevated levels of TNF-α have also been implicated in many other disorders and disease conditions, including cachexia, septic shock syndrome, osteoarthritis, inflammatory bowel diseases such as Crohn's disease and ulcerative colitis etc.

Elevated levels of TNF-α and/or IL-1 over basal levels have been implicated in mediating or exacerbating a number of disease states including rheumatoid arthritis; osteoporosis; multiple myeloma; uveititis; acute and chronic myelogenous leukemia; pancreatic β cell destruction; osteoarthritis; rheumatoid spondylitis; gouty arthritis; inflammatory bowel disease; adult respiratory distress syndrome (ARDS); psoriasis; Crohn's disease; allergic rhinitis; ulcerative colitis; anaphylaxis; contact dermatitis; asthma; muscle degeneration; cachexia; type I and type II diabetes; bone resorption diseases; ischemia reperfusion injury; atherosclerosis; brain trauma; multiple sclerosis; cerebral malaria; sepsis; septic shock; toxic shock syndrome; fever, and myalgias due to infection. HIV-1, HIV-2, HIV-3, cytomegalovirus (CMV), influenza, adenovirus, the herpes viruses (including HSV-1, HSV-2), and herpes zoster are also exacerbated by TNF-α.

It can be seen that inhibitors of TNF-α are potentially useful in the treatment of a wide variety of diseases. Compounds that inhibit TNF-α have been described in several patents. Excessive production of IL-6 is implicated in several disease states, and it is highly desirable to develop compounds that inhibit IL-6 secretion. Compounds that inhibit IL-6 have been described in U.S. Pat. Nos. 6,004,813, 5,527, 546 and 5,166,137.

The cytokine IL-1β also participates in the inflammatory response. It stimulates thymocyte proliferation, fibroblast growth factor activity, and the release of prostaglandins from synovial cells. Elevated or unregulated levels of the cytokine IL-1β have been associated with a number of inflammatory diseases and other disease states, including but not limited to adult respiratory distress syndrome, allergy, Alzheimer's disease etc. Since overproduction of IL-1β is associated with numerous disease conditions, it is desirable to develop compounds that inhibit the production or activity of IL-1β.

In rheumatoid arthritis models in animals, multiple intra-articular injections of IL-1 have led to an acute and destructive form of arthritis (Chandrasekhar et al., Clinical Immunol Immunopathol. 55, 382, 1990). In studies using cultured rheumatoid synovial cells, IL-1 is a more potent inducer of stromelysin than TNF-α. (Firestein, Am. J. Pathol. 140, 1309, 1992). At sites of local injection, neutrophil, lymphocyte, and monocyte emigration have been observed. The emigration is attributed to the induction of chemokines (e.g., IL-8), and the up-regulation of adhesion molecules (Dinarello, Eur. Cytokine Netw. 5, 517-531, 1994).

In rheumatoid arthritis, both IL-1 and TNF-α induce synoviocytes and chondrocytes to produce collagenase and neutral proteases, which leads to tissue destruction within the arthritic joints. In a model of arthritis (collagen-induced arthritis i.e.CIA in rats and mice) intra-articular administration of TNF-α either prior to or after the induction of CIA led to an accelerated onset of arthritis and a more severe course of the disease (Brahn et al., Lymphokine Cytokine Res. 11, 253, 1992; and Cooper, Clin. Exp. Immunol. 898, 244, 1992).

IL-8 has been implicated in exacerbating and/or causing many disease states in which massive neutrophil infiltration into the sites of inflammation or injury (e.g., ischemia) is mediated; chemotactic nature of IL-8, including, but is not limited to, the following: asthma, inflammatory bowel disease, psoriasis, adult respiratory distress syndrome, cardiac and renal reperfusion injury, thrombosis and glomerulonephritis. In addition to the chemotaxis effect on neutrophils, IL-8 also has the ability to activate neutrophils. Thus, reduction in IL-8 levels may lead to diminish, neutrophil infiltration.

It has been reported that Cyclooxygenase enzyme exists in three isoforms, namely, COX-1, COX-2 and COX-3. COX-1 enzyme is essential and primarily responsible for the regulation of gastric fluids, whereas COX-2 enzyme is present at the basal levels and is reported to have a major role in the prostaglandin synthesis for inflammatory response. These prostaglandins are known to cause inflammation in the body. Hence, if the synthesis of these prostaglandins is stopped by way of inhibiting COX-2 enzyme, inflammation and its related disorders can be treated. COX-3 possesses glycosylation-dependent cyclooxygenase activity. Comparison of canine COX-3 activity with murine COX-1 and COX-2 demonstrated, that this enzyme is selectively inhibited by analgesic/antipyretic drugs such as acetaminophen, phenacetin, antipyrine, dipyrone, and is potently inhibited by some non-steroidal anti-inflammatory drugs. Thus, inhibition of COX-3 could represent a primary central mechanism by which these drugs decrease pain and possibly fever. Earlier reports prior to Coxib's development show that inhibitors of COX-1 enzyme cause gastric ulcers, whereas selective COX-2 and COX-3 enzyme inhibitors are devoid of this function and hence are found to be safe. But, recent reports show that the selective COX-2 inhibitors (Coxib's) are associated with cardiovascular risks. So, inhibition of COX-2 without causing cardiovascular risks and gastric ulcers due to inhibition of COX-1 is shown to be safe and is concerned in the present invention.

Cardiovascular pathologies that remain the leading cause of mortality and morbidity in western society include several diseases, such as ishemic cardiopathy of which myocardial infarction represents the most important form. Ischemic cardiopathy is characterized by an inadequacy between supply and demand in oxygenated blood correlated with a diminution of coronary blood flow due to coronary artery stenosis or occlusion. This artery occlusion often caused by atherosclerous lesions, acute thrombosis, edema, ballooning of atheromatous plaque, or bleeding (Pearson et al., Am. J. Pathol, 86, 657-664, 1977; Horie et al, Br Heart J. 40: 153-161, 1978; Koenig, Cardiol. Review, 9:31-35, 2001). $TXA_2$ is a potent platelet activator and constrictor of vascular and bronchial smooth muscles. $TXA_2$ is a short live lipidic mediator generated by the cyclooxygenase pathway, is mainly produced by platelets, macrophages, and lung parenchyma. $TXA_2$ is a potent platelet activator and constrictor of vascular and bronchial smooth muscles. It has been demonstrated that drugs able to antagonize $TXA_2$ receptors or to inhibit thromboxane synthase (TS) reduce the severity of myocardial ischemia (Schror et al, Am. J. Physiol, 238: 87-92, 1980; Burke et al, Br J Clin Pharmacol, 15:97S-101S, 1983; Hock et al, Eur. J. Pharmacol, 122:213-219, 1986; Brezinsky et al, J. Cardiovasc Pharmacol, 9:65-71, 1987) and is also concerned in the present invention.

Few Prior Art References, which Disclose the Closest Compounds, are Given Below:

i) WO 2005/084368 discloses novel compounds of formula,

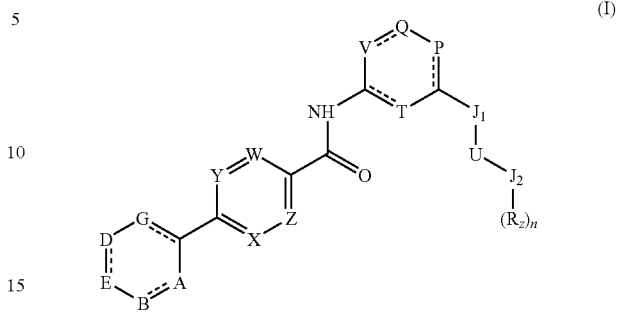

(I)

wherein, each ---- independently represents a single or double bond; either (a) A, B and E are independently $CR_1$, $C(R_1)_2$, $NR_1$ or N; or (b) B is joined with A or E to form a fused 5- to 8-membered partially satured ring that is substituted with 0 to 3 substituents, independently selected from $R_1$, and the other of A or E is $CR_1$, $C(R_1)_2$, $NR_1$, or N; D and G are independently $CR_1$, $C(R_1)_2$, $NR_1$; W, X, Y and Z are independently $CR_1$ and N; P, Q, T and V are independently $CR_1$, $C(R_1)_2$, N or NF; or Q is taken together with V or P to form a fused 5-to 7-membered carbocycle or heterocycle that is substituted with from 0 to 4 substitutents, independently chosen from $R_b$; $R_1$ is independently chosen at each occurrence from hydrogen, halogen, hydroxy, amino, cyano, nitro and groups of the formula L-M; L is independently chosen at each occurrence from a single covalent bond, O, C(=O), OC(=O), C(=O)O, OC(=O)O, $S(O)_m$, $N(R_x)$, C(=O)N $(R_x)$, $N(R_x)C(=O)$, $N(R_x)S(O)_m$, $S(O)_m N(R_x)$ and $N[S(O)_m R_x]S(O)_m$; wherein m is independently selected at each occurrence from 0, 1 and 2 and M is independently selected at each occurrence from (a) hydrogen; and (b) $C_1$-$C_8$ alkyl, $C_2$-$C_8$alkenyl, $C_2$-$C_8$alkynyl, mono- and di-($C_1$-$C_4$alkyl)amino$C_0$-$C_4$alkyl, phenyl$C_0$-$C_4$alkyl, $C_3$-$C_8$cycloalkyl$C_0$-$C_4$alkyl, (5-membered heteroaryl)$C_0$-$C_4$alkyl, and (5- to 7-membered heterocycloalkyl)$C_0$-$C_4$alkyl, each of which is substituted with from 0-5 substitutents independently selected from $R_b$; $J_1$ chosen form O, NH and S; U is $C_1$-$C_3$alkyl, substituted with from 0 to 3 substitutents independently chosen from oxo and $C_1$-$C_3$alkyl, or two substitents are taken together to form a 3- to 7-membered cycloalkyl or heterocycloalyl. The invention further relates to the use of such compounds for treating conditions related to capsaicin receptor activation, for identifying other agents that bind to capsaicin receptor, and as probes for the detection and localization of capsaicin receptor. An example of these compounds is shown below in formula (1)

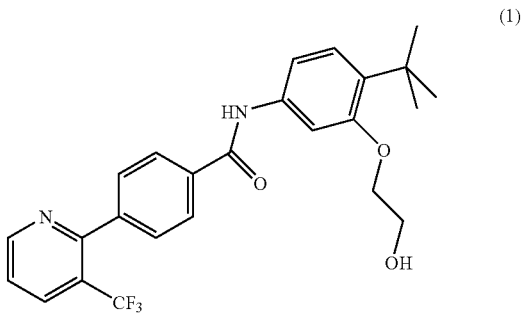

(1)

ii) U.S. Pat. No. 5,811,428 discloses the following general structure,

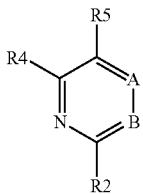

wherein A is C—R$_6$ when B is N, and A is N when B is C—R$_1$, and wherein R$_1$, R$_2$, R$_4$, R$_5$ and R$_6$ are as defined below. Thus, when A is C—R$_6$ and B is N, structure (I) is a pyrimidine-containing compound having structure (II), and when A is N and B is C—R$_1$, structure (I) is a pyrazine containing compound having structure (III). The inventions relates generally to compounds that block intracellular signal transduction and activation of transcription factors, and to methods for preventing or treating immunoinflammatory and autoimmune diseases.

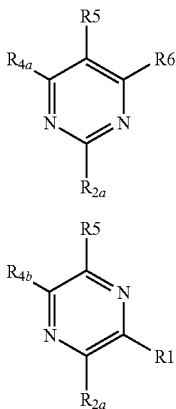

(II)

(III)

Examples of these compounds are shown below,

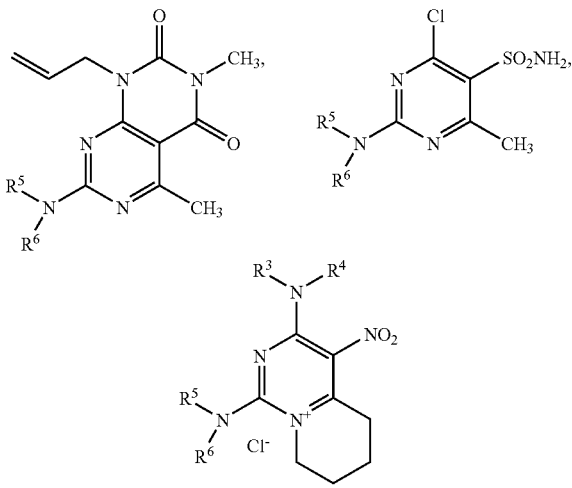

iii) U.S. Pat. No. 6,835,726 discloses the following general structure, in which X represents —NR$^3$R$^4$, —OR$^3$, —SR$^3$, aryl, alkyl or arylakyl. The letter Y represents a covalent bond, —N(R$^6$)—, —O—, —S—, —C(=O)— or an alkylene group. R$^1$ and R$^2$ are independently selected from hydrogen, alkyl, —O-alkyl, —S-alkyl, aryl, arylalkyl, —O-aryl, —S-aryl, —NO$_2$, —NR$^7$R$^8$, —C(O)R$^9$, —CO$_2$R$^{10}$, —C(O)NR$^7$R$^8$, —N(R$^7$)C(O)R$^9$, —N(R$^7$)CO$_2$R$^{11}$, —N(R$^9$)C(O)NR$^7$R$^8$, —S(O)$_m$NR$^7$R$^8$, —S(O)$_n$R$^9$, —CN, halogen, and —N(R$^7$)S(O)$_m$R$^{11}$. R$^5$ and R$^6$ are independently hydrogen, alkyl, aryl or aralkyl. Compounds and compositions are provided which are useful for the treatment of viral infections particularly human cytomegalovirus infection.

Examples of these compounds are shown below,

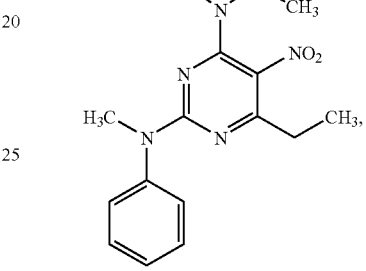

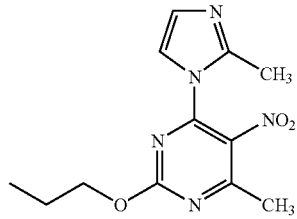

iv) US 2005/0065145 A1 discloses DPP-IV inhibitors of the following general structure:

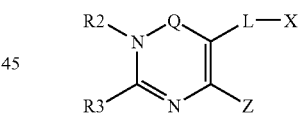

wherein, Q is selected from the group consisting of CO, SO, SO$_2$, and C=NR$_4$; Z is a leaving group, selected from the group consisting of halo, perhalo (C$_{1-10}$) alkyl, amino, cyano, thio, (C$_{1-10}$)alkyl, cycloalkyl, heterocycloalkyl, aryl, heteroaryl, carbonyl (C$_{1-3}$)alkyl, thiocarbonyl (C$_{1-3}$) alkyl, sulfonyl (C$_{1-3}$)alkyl, sulfinyl (C$_{1-3}$)alkyl, imino (C$_{1-3}$)alkyl, hydroxy, alkoxy, aryloxy, heteroaryloxy, alkenyl, alkynyl, carbonyl group, imino group, sulfonyl group and sulfinyl group, each substituted or unsubstituted, and a substituted or unsubstituted 4, 5, 6, or 7 membered ring; R$_2$ is selected from the group consisting of hydrogen, (C$_{1-10}$) alkyl, (C$_{3-12}$)cycloalkyl, (C$_{3-12}$)cycloalkyl(C$_{1-5}$)alkyl, hetero(C$_{3-12}$)cycloalkyl, hetero(C$_{3-12}$)cycloalkyl(C$_{1-5}$)alkyl, aryl(C$_{1-10}$)alkyl, heteroaryl(C$_{1-5}$)alkyl, (C$_{9-12}$)bicycloaryl, (C$_{9-12}$)bicycloaryl(C$_{1-5}$)alkyl, hetero(C$_{4-12}$)bicycloaryl, hetero(C$_{8-12}$)bicycloaryl(C$_{1-5}$)alkyl, carbonyl (C$_{1-3}$)alkyl, thiocarbonyl (C$_{1-3}$)alkyl, sulfonyl (C$_{1-3}$)alkyl, sulfinyl (C$_{1-3}$)alkyl, imino (C$_{1-3}$)alkyl, amino, aryl, heteroaryl, hydroxy, alkoxy, aryloxy, heteroaryloxy, carbonyl group, imino group, sulfonyl group and sulfinyl group, each substituted or unsubstituted, with the proviso that $R_2$ is not NH or N=CH; $R_3$ is selected from the group consisting of hydrogen, halo, perhalo($C_{1-10}$)alkyl, amino, cyano, nitro, thio, ($C_{1-10}$)alkyl, ($C_{3-12}$)cycloalkyl, hetero($C_{3-12}$)cycloalkyl, aryl($C_{1-10}$)alkyl, heteroaryl ($C_{1-5}$)alkyl, ($C_{9-12}$)bicycloaryl, hetero($C_{8-12}$)bicycloaryl, carbonyl ($C_{1-3}$) alkyl, thiocarbonyl ($C_{1-3}$)alkyl, sulfonyl ($C_{1-3}$)alkyl, sulfinyl ($C_{1-3}$)alkyl, imino ($C_{1-3}$)alkyl, aryl, heteroaryl, hydroxy, alkoxy, aryloxy, heteroaryloxy, alkenyl, alkynyl, carbonyl group, imino group, sulfonyl group and sulfinyl group, each substituted or unsubstituted, or where $R_2$ and $R_3$ are taken together to form a ring; $R_4$ is selected from the group consisting of hydrogen, ($C_{1-10}$)alkyl, cycloalkyl, heterocycloalkyl, aryl, heteroaryl, arylalkyl, heteroarylalkyl, bicycloaryl, heterobicycloaryl, each substituted or unsubstituted; L is a linker providing 0-6 atom separation between X and the ring to which L is attached; X is selected from the group consisting of ($C_{1-10}$)alkyl, ($C_{3-12}$)cycloalkyl, hetero($C_{3-12}$)cycloalkyl, aryl($C_{1-10}$)alkyl, heteroaryl($C_{1-5}$)alkyl, ($C_{9-12}$)bicycloaryl, hetero($C_{4-12}$)bicycloaryl, carbonyl ($C_{1-3}$)alkyl, thiocarbonyl ($C_{1-3}$)alkyl, sulfonyl ($C_{1-3}$)alkyl, sulfinyl ($C_{1-3}$)alkyl, imino ($C_{1-3}$) alkyl, amino, aryl, heteroaryl, hydroxy, alkoxy, aryloxy, heteroaryloxy, alkenyl, alkynyl, carbonyl group, cyano, imino group, sulfonyl group and sulfinyl group, each substituted or unsubstituted.

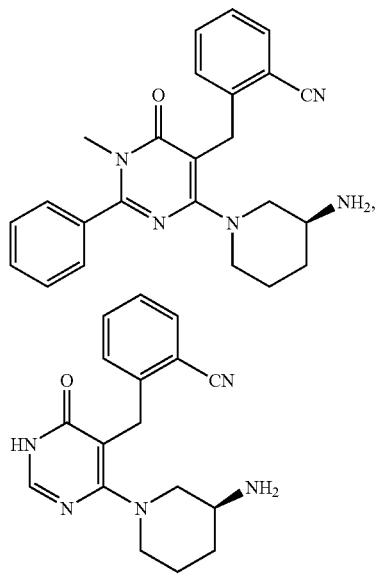

OBJECTIVE OF THE INVENTION

We have focused our research to identify cytokine inhibitors, predominantly acting through the inhibition of TNF-α, which are devoid of any side effects normally associated with TNF-α inhibitors or/blockers. Our sustained efforts have resulted in novel compounds of the formula (I). The derivatives may be useful in the treatment of inflammation and immunological diseases. Particularly the compounds of the present invention are useful for the treatment of immunological diseases those mediated by cytokines such as TNF-α, IL-1, IL-6, IL-1β, IL-8, IL-12 and inflammation. The compounds of the present invention are also useful in the treatment of rheumatoid arthritis; osteoporosis; multiple myeloma; uveititis; acute and chronic myelogenous leukemia; ischemic heart disease; atherosclerosis; cancer; ischemic-induced cell damage; pancreatic β-cell destruction; osteoarthritis; rheumatoid spondylitis; gouty arthritis; inflammatory bowel disease; adult respiratory distress syndrome; psoriasis; Crohn's disease; allergic rhinitis; ulcerative colitis; anaphylaxis; contact dermatitis; asthma; muscle degeneration; cachexia; bone resorption diseases; ischemia reperfusion injury; brain trauma; multiple sclerosis; sepsis; septic shock; toxic shock syndrome; fever, and myalgias due to infection.

SUMMARY OF THE INVENTION

The present invention relates to novel compounds of the formula (I),

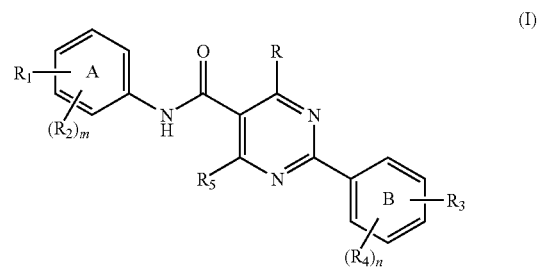

their derivatives, analogs, tautomeric forms, stereoisomers, polymorphs, hydrates, solvates, and pharmaceutically acceptable salts and compositions; wherein rings represented by A is selected from aryl or heteroaryl; wherein rings represented by B is selected from aryl or heteroaryl; R independently represents hydrogen, hydroxyl, amino, azido, alkyl, alkyloxy, aryloxy, heteroaryloxy, $SR_6$, $S(O)_pR_7$, haloalkyl, aminocycloalkyl, aminoalkyl, aminodialkyl, —NH($C_1$-$C_5$)$_n$—X, X represents aryl, heteroaryl, heterocyclyl, aminoheterocyclyl; aminoalkanols represent —NH—($CH_2$)$_q$OH (the methylene group may be further substituted for e.g. by alkyl, —OH and the like); hydrazine, alkylhydrazine; $R_1$ independently represents hydrogen, $SR_6$ and $S(O)_pR_7$; $R_2$ independently represents hydrogen, hydroxyl, halogen, nitro, cyano, azido, amino, alkyl, haloalkyl, alkoxy, aminoalkyl, aminodialkyl, aminoacyl, alkoxycarbonyl, alkoxyalkyl groups, $COR_8$, carboxylic acid and its derivatives; $R_3$ independently represents hydrogen, $SR_6$ and_$S(O)_pR_7$; $R_4$ independently represents hydrogen, hydroxyl, halogen, nitro, cyano, azido, amino, alkyl, haloalkyl, alkoxy, aminoalkyl, aminodialkyl, aminoacyl, alkoxycarbonyl, alkoxyalkyl groups, $COR_8$, carboxylic acid and its derivatives; $R_5$ independently represents hydrogen, hydroxyl, amino, azido, alkyl, alkyloxy, aryloxy, heteroaryloxy, $SR_6$, $S(O)_pR_7$, haloalkyl, aminocycloalkyl, aminoalkyl, aminodialkyl, —NH($C_1$-$C_5$)$_n$—X, X represents aryl, heteroaryl, heterocyclyl, aminoheterocyclyl; aminoalkanols represent —NH—($CH_2$)$_q$OH, hydrazine, alkylhydrazine; $R_6$ represents hydrogen, alkyl, aryl, alkylhalide, alkylester; $R_7$ represents amino, hydroxyl, hydrazine, halogen, alkyl, alkylhydrazine, acylhydrazide, aminoacyl, aryl, aminoaryl, aminoheteroaryl, aminoheterocyclyl; $R_8$ represents hydrogen, hydroxyl, amino, halogen, alkyl, haloalkyl, alkoxy, aryloxy, aminoalkyl, dialkylamino, arylamino, heteroarylamino, acylamino; m and n is an integer in the range of 0 to 4, p is an integer in the range of 1 to 2 and q is an integer in the range of 1 to 10.

The foregoing merely summarizes certain aspects of the invention and is not intended, nor should it be construed, as limiting the invention in any way. All patents and other publications recited herein are hereby incorporated by reference in their entirety.

DETAILED DESCRIPTION OF THE INVENTION

The present invention relates to novel compounds of the formula (I),

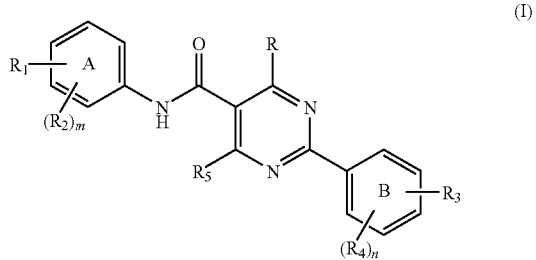

their derivatives, analogs, tautomeric forms, stereoisomers, polymorphs, hydrates, solvates, and pharmaceutically acceptable salts and compositions; wherein suitable ring systems represented by A is selected from phenyl, naphthyl, pyridyl, thienyl, pyrimidinyl, and the like which may be substituted. Suitable ring systems represented by B is selected from phenyl, naphthyl, pyridyl, thienyl, pyrimidinyl, and the like which may be substituted.

R independently represents hydrogen, halogen (such as fluorine, chlorine, bromine, iodine), hydroxyl, azido, amino, linear or branched ($C_1$-$C_4$) alkyl groups, such as methyl, ethyl, n-propyl, isopropyl, n-butyl and the like; haloalkyl groups such as chloromethyl, chloroethyl, trifluoromethyl, trifluoroethyl, dichloromethyl, dichloroethyl and the like; $SR_6$, $S(O)_qR_7$; aminocycloalkyl groups such as —NH-cylcopropyl, —NH-cyclopentyl, —NH-cyclohexyl and the like; monoalkylamino groups such as —$NHCH_3$, —$NHC_2H_5$, —$NHC_3H_7$, —$NHC_6H_{13}$, and the like, which may be substituted; dialkylamino groups such as —$N(CH_3)_2$, —$NCH_3(C_2H_5)$, —$N(C_2H_5)_2$ and the like; —$NH(C_1$-$C_5)_n$—X, wherein linear or branched ($C_1$-$C_5$) alkyl groups, such as methyl, ethyl, n-propyl, isopropyl, n-butyl and the like; X is aryl or heteroaryl, aryl groups such as phenyl, naphthyl and the like and heteroaryl groups such as pyridyl, thienyl, furyl, pyrrolyl, oxazolyl, thiazolyl, imidazolyl, isooxazolyl, oxadiazolyl, triazolyl, thiadiazolyl, tetrazolyl, pyrimidinyl, benzopyranyl, benzofuranyl, benzimidazolyl, benzoxazolyl, benzothiazolyl, benzopyrrolyl, benzoxadiazolyl, benzothiadiazolyl and the like; heterocyclyl groups such as pyrrolidinyl, morpholinyl, thiomorpholinyl, piperidinyl, piperazinyl, and the like; aminoheterocyclyl groups such as aminopiperazinyl, and the like; aminoalkanols such as —NH—$(CH_2)_q$OH (the methylene group may be further substituted for e.g. by alkyl, —OH and the like); hydrazine; alkylhydrazines such as —$N(CH_3)NH_2$, —$N(C_2H_5)NH_2$, —$N(C_3H_7)NH_2$ and the like.

Suitable groups represented by $R_1$ are selected from hydrogen, $SR_6$ and $S(O)_pR_7$.

Suitable groups represented by $R_2$ are selected from hydrogen, hydroxyl, halogen atoms such as fluorine, chlorine, bromine, iodine; hydroxyl, nitro, cyano, azido, amino, linear or branched ($C_1$-$C_4$) alkyl groups such as methyl, ethyl, n-propyl, isopropyl, n-butyl and the like; haloalkyl groups such as chloromethyl, chloroethyl, trifluoromethyl, trifluoroethyl, dichloromethyl, dichloroethyl and the like; linear or branched ($C_1$-$C_6$) alkoxy groups, such as methoxy, ethoxy, n-propoxy, isopropoxy and the like; aminoalkyl groups such as —$NHCH_3$, —$NHC_2H_5$, —$NHC_3H_7$ and the like; aminodialkyl groups such as —$N(CH_3)_2$, —$NCH_3(C_2H_5)$, —$N(C_2H_5)_2$ and the like; acyl groups such as —C(=O)$CH_3$, —C(=O)$CF_3$, —C(=O)$C_2H_5$, —C(=O)$C_3H_7$, —C(=S)$CH_3$, —C(=S)$CF_3$, —C(=S)$C_2H_5$, —C(=S)$C_3H_7$, benzoyl; aminoacyl groups such as —NHC(=O)$CH_3$, —NHC(=O)$CF_3$, —NHC(=O)$C_2H_5$, —NHC(=O)$C_3H_7$, and the like; alkoxycarbonyl groups such as methoxycarbonyl, ethoxycarbonyl, n-propoxycarbonyl, isopropoxycarbonyl and the like; alkoxyalkyl groups such as methoxymethyl, ethoxymethyl, methoxyethyl, ethoxyethyl and the like; $COR_8$; carboxylic acid and its derivatives such as esters, amides, acid halides and the like.

Suitable groups represented by $R_3$ are selected from hydrogen, $SR_6$ and $S(O)_pR_7$.

Suitable groups represented by $R_4$ are selected from hydrogen, hydroxyl, halogen atoms such as fluorine, chlorine, bromine, iodine; hydroxyl, nitro, cyano, azido, amino, linear or branched ($C_1$-$C_4$) alkyl groups such as methyl, ethyl, n-propyl, isopropyl, n-butyl and the like; haloalkyl groups such as chloromethyl, chloroethyl, trifluoromethyl, trifluoroethyl, dichloromethyl, dichloroethyl and the like; linear or branched ($C_1$-$C_6$) alkoxy groups, such as methoxy, ethoxy, n-propoxy, isopropoxy and the like; aminoalkyl groups such as —$NHCH_3$, —$NHC_2H_5$, —$NHC_3H_7$ and the like; aminodialkyl groups such as —$N(CH_3)_2$, —$NCH_3(C_2H_5)$, —$N(C_2H_5)_2$ and the like; acyl groups such as —C(=O)$CH_3$, —C(=O)$CF_3$, —C(=O)$C_2H_5$, —C(=O)$C_3H_7$, —C(=S)$CH_3$, —C(=S)$CF_3$, —C(=S)$C_2H_5$, —C(=S)$C_3H_7$, benzoyl; aminoacyl groups such as —NHC(=O)$CH_3$, —NHC(=O)$CF_3$, —NHC(=O)$C_2H_5$, —NHC(=O)$C_3H_7$, and the like; alkoxycarbonyl groups such as methoxycarbonyl, ethoxycarbonyl, n-propoxycarbonyl, isopropoxycarbonyl and the like; alkoxyalkyl groups such as methoxymethyl, ethoxymethyl, methoxyethyl, ethoxyethyl and the like; $COR_8$; carboxylic acid and its derivatives such as esters, amides, acid halides and the like.

$R_5$ independently represents hydrogen, hydroxyl, azido, amino, linear or branched ($C_1$-$C_4$) alkyl groups such as methyl, ethyl, n-propyl, isopropyl, n-butyl and the like; haloalkyl groups such as chloromethyl, chloroethyl, trifluoromethyl, trifluoroethyl, dichloromethyl, dichloroethyl and the like; $SR_6$, $S(O)_qR_7$; aminocycloalkyl groups such as —NH-cylcopropyl, —NH-cyclopentyl, —NH-cyclohexyl and the like; monoalkylamino groups such as —$NHCH_3$, —$NHC_2H_5$, —$NHC_3H_7$, —$NHC_6H_{13}$, and the like, which may be substituted; dialkylamino groups such as —$N(CH_3)_2$, —$NCH_3(C_2H_5)$, —$N(C_2H_5)_2$ and the like; —$NH(C_1$-$C_5)_n$—X, wherein linear or branched ($C_1$-$C_5$) alkyl groups, such as methyl, ethyl, n-propyl, isopropyl, n-butyl and the like; X is aryl or heteroaryl, aryl groups such as phenyl, naphthyl and the like and heteroaryl groups such as pyridyl, thienyl, furyl, pyrrolyl, oxazolyl, thiazolyl, imidazolyl, isooxazolyl, oxadiazolyl, triazolyl, thiadiazolyl, tetrazolyl, pyrimidinyl, benzopyranyl, benzofuranyl, benzimidazolyl, benzoxazolyl, benzothiazolyl, benzopyrrolyl, benzoxadiazolyl, benzothiadiazolyl and the like; heterocyclyl groups such as pyrrolidinyl, morpholinyl, thiomorpholinyl, piperidinyl, piperazinyl, and the like; aminoheterocyclyl groups such as aminopiperazinyl, and the like; aminoalkanols such as —NH—$(CH_2)_q$OH; hydrazine; alkylhydrazines such as —$N(CH_3)NH_2$, —$N(C_2H_5)NH_2$, —$N(C_3H_7)NH_2$ and the like.

Suitable groups represented by $R_6$ are selected from hydrogen, linear or branched ($C_1$-$C_6$) alkyl groups, such as methyl, ethyl, n-propyl, isopropyl, n-butyl, isobutyl, t-butyl, n-pentyl, isopentyl, hexyl and the like; aryl groups such as phenyl, naphthyl and the like; alkylhalides such as —$CH_2Cl$, —$CH_2CH_2Cl$ and the like; alkylesters such as —$CH_2OCOC_2H_5$, —$CH_2OCOC_3H_7$ and the like.

Suitable groups represented by $R_7$ are selected from amino, hydroxyl, hydrazine, halogen atoms such as fluorine, chlorine, bromine, iodine; linear or branched ($C_1$-$C_6$) alkyl groups, such as methyl, ethyl, n-propyl, isopropyl, n-butyl, isobutyl, t-butyl, n-pentyl, isopentyl, hexyl and the like; alkylhydrazine groups such as —$N(CH_3)NH_2$, —$N(C_2H_5)NH_2$ and the like; acylhydrazide groups as —$NHNH(C=O)CH_3$, —$NHNH(C=O)CF_3$ and the like; aminoacyl groups such as —$NHC(=O)CH_3$, —$NHC(=O)CF_3$, —$NHC(=O)C_2H_5$, —$NHC(=O)C_3H_7$, —$NHC(=O)C_6H_{13}$; aminoalkanols such as —$NH$—$(CH_2)_qOH$; aryl groups such as phenyl, naphthyl and the like; aminoaryl groups such as phenyl amino, naphthyl amino and the like; aminoheteroaryl groups such as thienylamino, pyridylamino, pyrimidyl amino and the like; aminoheterocyclyl groups such as aminopiperazine, aminomorpholine and the like.

Suitable groups represented by $R_8$ are selected from hydrogen, hydroxyl, amino, halogen atoms such as fluorine, chlorine, bromine, iodine; linear or branched ($C_1$-$C_4$) alkyl groups, such as methyl, ethyl, n-propyl, isopropyl, n-butyl, isobutyl, t-butyl, and the like; haloalkyl groups such as chloromethyl, chloroethyl, trifluoromethyl, trifluoroethyl, dichloromethyl, dichloroethyl and the like; linear or branched ($C_1$-$C_4$) alkoxy groups, such as methoxy, ethoxy, n-propoxy, isopropoxy and the like; aryloxy groups such as phenoxy, napthoxy and the like; aminoalkyl groups such as —$NHCH_3$, —$NHC_2H_5$, —$NHC_3H_7$, —$NHC_6H_{13}$, and the like, which may be substituted; dialkylamino groups such as —$N(CH_3)_2$, —$NCH_3(C_2H_5)$, —$N(C_2H_5)_2$ and the like; arylamino groups such as phenyl amino, naphthyl amino and the like; heteroarylamino groups such as thienylamino, pyridylamino, pyrimidyl amino and the like, acylamino groups such as —$NHC(=O)CH_3$, —$NHC(=O)CF_3$, —$NHC(=O)C_2H_5$, —$NHC(=O)C_3H_7$, —$NHC(=O)C_6H_{13}$ and the like.

m and n are integers ranging from 0 to 4; p is an integer of 1 or 2; q is an integer in the range of 1 to 10.

When the groups R, $R_1$, $R_2$, $R_3$, $R_4$ and $R_5$ are substituted, the term substituted means that one or more hydrogen atoms are replaced by a substituent including, but not limited to, halogen, hydroxy, nitro, cyano, azido, nitroso, amino, amidino, hydrazine, formyl, alkyl, aryl, cycloalkyl, alkoxy, aryloxy (e.g., phenoxy), aralkyl (e.g., benzyl), aralkoxy (e.g., benzyloxy), acyl, acyloxyacyl, carboalkoxy (e.g., acyloxy), carboxyalkyl (e.g., esters), carboxamido, aminocarbonyl, carbonyl, alkylenedioxy, heterocyclyl, heteroaryl, heteroaralkyl, heteroaryloxy, heteroaralkoxy, monoalkylamino, dialkylamino, acylamino, alkoxycarbonyl, aryloxycarbonyl, alkylsulfonyl, arylsulfonyl, alkylsulfinyl, arylsulfinyl, alkylthio, arylthio, sulfanyl, sulfinyl, sulfonyl, sulfamoyl, thio, alkoxyalkyl groups, carboxylic acids and its derivatives. In addition, the substituent may be substituted.

Furthermore when A and B are cyclic rings, they represent substituted or unsubstituted 5 to 10 membered ring systems, and also the rings may be monocyclic or bicyclic, saturated, partially saturated or aromatic, containing 1 to 4 hetero atoms selected from O, S and N and the like.

The term analog includes a compound, which differs from the parent structure by one or more C, N, O or S atoms. Hence, a compound in which one of the N atoms in the parent structure is replaced by an S atom is an analog of the former.

The term stereoisomer includes isomers that differ from one another in the way the atoms are arranged in space, but whose chemical formulas and structures are otherwise identical. Stereoisomers include enantiomers and diastereoisomers.

The term tautomers include readily interconvertible isomeric forms of a compound in equilibrium. The enol-keto tautomerism is an example.

The term polymorphs include crystallographically distinct forms of compounds with chemically identical structures.

The term pharmaceutically acceptable solvates includes combinations of solvent molecules with molecules or ions of the solute compound.

The term derivative refers to a compound obtained from a compound according to formula (I), an analog, tautomeric form, stereoisomer, polymorph, hydrate, pharmaceutically acceptable salt or pharmaceutically acceptable solvate thereof, by a simple chemical process converting one or more functional groups, such as, by oxidation, hydrogenation, alkylation, esterification, halogenation, and the like.

Pharmaceutically acceptable salts of the present invention include alkali metal salts like Li, Na, and K salts, alkaline earth metal salts like Ca and Mg salts, salts of organic bases such as diethanolamine, α-phenylethylamine, benzylamine, piperidine, morpholine, pyridine, hydroxyethylpyrrolidine, hydroxyethylpiperidine, guanidine, choline and the like, ammonium or substituted ammonium salts, aluminum salts. Salts also include amino acid salts such as glycine, alanine, cysteine, lysine, arginine, phenylalanine etc. Salts may include sulphates, nitrates, phosphates, perchlorates, borates, hydrohalides, acetates, tartrates, maleates, citrates, succinates, oxalates, palmoates, methanesulphonates, tosylates, benzoates, salicylates, hydroxynaphthoates, benzenesulfonates, ascorbates, glycerophosphates, ketoglutarates and the like. Pharmaceutically acceptable solvates may be hydrates or comprising of other solvents of crystallization such as alcohols.

Particularly Useful Compounds According to the Present Invention Include:

1. 4-Hydroxy-N-(4-methylphenyl)-6-(methylthio)-2-[4-(methylthio)phenyl]pyrimidine-5-carboxamide;
2. 4-Hydroxy-N-(3,4-dimethylphenyl)-6-(methylthio)-2-[4-(methylthio)phenyl]pyrimidine-5-carboxamide;
3. 2-(4-Fluorophenyl)-4-hydroxy-6-(methylthio)-N-[4-(methylthio)phenyl]pyrimidine-5-carboxamide;
4. 4-Chloro-N-(4-methylphenyl)-6-(methylthio)-2-[4-(methylthio) phenyl]pyrimidine-5-carboxamide;
5. 4-(Methylamino)-N-(4-methylphenyl)-6-(methylthio)-2-[4-(methylthio)phenyl]pyrimidine-5-carboxamide;
6. N-(4-Methoxyphenyl)-4-(methylamino)-6-(methylthio)-2-pyridin-3-ylpyrimidine-5-carboxamide;
7. N-(3,4-Dimethylphenyl)-4,6-bis(methylamino)-2-pyridin-3-ylpyrimidine-5-carboxamide;
8. N-(4-Ethylphenyl)-4-(methylamino)-6-(methylthio)-2-[4-(methylthio)phenyl]pyrimidine-5-carboxamide;
9. N-(3,4-Dimethylphenyl)-4-(methylamino)-6-(methylthio)-2-[4-(methylthio)phenyl]pyrimidine-5-carboxamide;
10. 2-[4-(Aminosulfonyl)phenyl]-4,6-bis(methylamino)-N-(3,4-dimethylphenyl)pyrimidine-5-carboxamide;
11. 2-[4-(Aminosulfonyl)phenyl]-N-(3,4-dimethylphenyl)-4-(methylamino)-6-(methylthio)pyrimidine-5-carboxamide;
12. 2-[4-(Aminosulfonyl)phenyl]-4-(methylamino)-N-(4-methylphenyl)-6-(methylthio)pyrimidine-5-carboxamide;

13. 2-[4-(Aminosulfonyl)phenyl]-4,6-bis(methylamino)-N-(4-methylphenyl)pyrimidine-5-carboxamide;
14. N-(4-Methoxyphenyl)-4-(methylamino)-6-(methylthio)-2-pyridin-4-ylpyrimidine-5-carboxamide;
15. N-(4-Ethoxyphenyl)-4,6-bis(methylamino)-2-pyridin-4-ylpyrimidine-5-carboxamide;
16. 2-[4-(Aminosulfonyl)phenyl]-4,6-bis(methylamino)-N-(4-ethylphenyl)pyrimidine-5-carboxamide;
17. 2-[4-(Aminosulfonyl)phenyl]-N-(4-ethylphenyl)-4-(methylamino)-6-(methylthio)pyrimidine-5-carboxamide;
18. N-(4-Fluorophenyl)-4-(methylamino)-6-(methylthio)-2-pyridin-4-ylpyrimidine-5-carboxamide;
19. 4-(Methylamino)-2-[4-(methylsulfinyl)phenyl]-N-(4-methoxyphenyl)-6-(methylthio)pyrimidine-5-carboxamide;
20. 4-(Methylamino)-N-(4-methoxyphenyl)-6-(methylthio)-2-[4-(methylthio)phenyl]pyrimidine-5-carboxamide;
21. N-(4-Ethylphenyl)-4-(methylamino)-6-(methylthio)-2-pyridin-4-ylpyrimidine-5-carboxamide;
22. N-(4-Ethylphenyl)-4-(methylamino)-6-(methylthio)-2-pyridin-3-ylpyrimidine-5-carboxamide;
23. 4-[(2-Hydroxyethyl)amino]-N-(4-methoxyphenyl)-6-(methylthio)-2-pyridin-3-ylpyrimidine-5-carboxamide;
24. 4-(Methylamino)-N-(4-methylphenyl)-6-(methylthio)-2-pyridin-4-ylpyrimidine-5-carboxamide;
25. N-(3,4-Dimethylphenyl)-4-(methylamino)-6-(methylthio)-2-pyridin-4-ylpyrimidine-5-carboxamide;
26. N-(3,4-Dimethylphenyl)-4,6-bis(methylamino)-2-pyridin-4-ylpyrimidine-5-carboxamide;
27. 4,6-Bis(methylamino)-N-(4-methylphenyl)-2-pyridin-4-ylpyrimidine-5-carboxamide;
28. N-(4-Methoxyphenyl)-4,6-bis(methylamino)-2-pyridin-3-ylpyrimidine-5-carboxamide;
29. N-(4-Fluorophenyl)-4-[(2-hydroxyethyl)amino]-6-(methylthio)-2-pyridin-4-ylpyrimidine-5-carboxamide;
30. 4-[(2-Hydroxyethyl)amino]-N-(4-methoxyphenyl)-6-(methylthio)-2-[4-(methylthio)phenyl]pyrimidine-5-carboxamide;
31. N-(4-Ethylphenyl)-4-[(2-hydroxyethyl)amino]-6-(methylthio)-2-pyridin-4-ylpyrimidine-5-carboxamide;
32. N-(3,4-Dimethylphenyl)-4-[(2-hydroxyethyl)amino]-6-(methylthio)-2-[4-(methylthio)phenyl]pyrimidine-5-carboxamide;
33. N-(4-Isoproylphenyl)-4-(methylamino)-6-(methylthio)-2-pyridin-3-ylpyrimidine-5-carboxamide;
34. N-(4-Isoproylphenyl)-4-(methylamino)-6-(methylthio)-2-pyridin-4-ylpyrimidine-5-carboxamide;
35. 4-[(2-Hydroxyethyl)amino]-N-(4-methylphenyl)-6-(methylthio)-2-pyridin-4-ylpyrimidine-5-carboxamide;
36. N-(4-Butylphenyl)-4-[(2-hydroxyethyl)amino]-6-(methylthio)-2-[4-(methylthio)phenyl]pyrimidine-5-carboxamide;
37. N-(3,4-Dimethylphenyl)-4-[(2-hydroxyethyl)amino]-6-(methylthio)-2-pyridin-4-ylpyrimidine-5-carboxamide;
38. 4-(Methylamino)-6-(methylthio)-N,2-bis[4-(methylthio)phenyl]pyrimidine-5-carboxamide;
39. N-(2,4-Dimethylphenyl)-4-(methylamino)-6-(methylthio)-2-[4-(methylthio)phenyl]pyrimidine-5-carboxamide;
40. N-(4-Ethoxyphenyl)-4-(methylamino)-6-(methylthio)-2-[4-(methylthio)phenyl]pyrimidine-5-carboxamide;
41. 4-Chloro-N-(3,4-dimethylphenyl)-6-(methylthio)-2-[4-(methylthio)phenyl]pyrimidine-5-carboxamide;
42. N-(3,4-Dimethylphenyl)-6-(methylthio)-2-[4-(methylthio)phenyl]-4-piperazin-1-ylpyrimidine-5-carboxamide;
43. 4-(Benzylamino)-N-(3,4-dimethylphenyl)-6-(methylthio)-2-[4-(methylthio)phenyl]pyrimidine-5-carboxamide;
44. N-(3,4-Dimethylphenyl)-4-(4-methylpiperazin-1-yl)-6-(methylthio)-2-[4-(methylthio)phenyl]pyrimidine-5-carboxamide;
45. 2-(4-Fluorophenyl)-4-(methylamino)-6-(methylthio)-N-[4-(methylthio)phenyl]pyrimidine-5-carboxamide;
46. N-(4-Bromophenyl)-4-[(2-hydroxyethyl)amino]-6-(methylthio)-2-pyridin-4-ylpyrimidine-5-carboxamide;
47. N-(4-Chlorophenyl)-4-[(2-hydroxyethyl)amino]-6-(methylthio)-2-pyridin-4-ylpyrimidine-5-carboxamide;
48. N-(3,4-Dimethylphenyl)-4-hydrazino-6-(methylthio)-2-[4-(methylthio)phenyl]pyrimidine-5-carboxamide;
49. N-(2,4-Dimethylphenyl)-4-[(2-hydroxyethyl)amino]-6-(methylthio)-2-pyridin--4-ylpyrimidine-5-carboxamide;
50. N-(3,4-Difluorophenyl)-4-[(2-hydroxyethyl)amino]-6-(methylthio)-2-[4-(methylthio)phenyl]pyrimidine-5-carboxamide;
51. 4-[Ethyl(hydroxymethyl)amino]-N-(4-methylphenyl)-6-(methylthio)-2-pyridin-4-ylpyrimidine-5-carboxamide;
52. N-(3,4-Difluorophenyl)-4-(methylamino)-6-(methylthio)-2-[4-(methylthio)phenyl]pyrimidine-5-carboxamide;
53. 2-(3-Fluorophenyl)-4-[(2-hydroxyethyl)amino]-6-(methylthio)-N-[(4-methylthio)phenyl]pyrimidine-5-carboxamide;
54. N-(3,4-Difluorophenyl)-2-(4-ethoxyphenyl)-4-[(2-hydroxyethyl)amino]-6-(methylthio)pyrimidine-5-carboxamide;
55. 4-[(2-Hydroxyethyl)amino]-N-(4-methoxyphenyl)-6-(methylthio)-2-pyridin-4-ylpyrimidine-5-carboxamide;
56. N-(4-Fluorophenyl)-4-{[1-(hydroxymethyl)propyl]amino}-6-(methylthio)-2-pyridin-4-ylpyrimidine-5-carboxamide;
57. 2-[4-(Dimethylamino)phenyl]-4-(methylamino)-N-(4-methoxyphenyl)-6-(methylthio)pyrimidine-5-carboxamide;
58. N-(3,4-Dimethylphenyl)-4-[(2-hydroxyethyl)amino]-2-(4-{[(2-hydroxyethyl)amino]sulfonyl}phenyl)-6-(methylthio)pyrimidine-5-carboxamide;
59. N-(4-Methoxyphenyl)-4-(methylamino)-6-(methylthio)-2-pyridin-3-ylpyrimidine-5-carboxamide orthophosphoric acid salt;
60. N-(4-Methoxyphenyl)-4-(methylamino)-6-(methylthio)-2-pyridin-3-ylpyrimidine-5-carboxamide hydrochloric acid salt;
61. N-(4-Methoxyphenyl)-4-(methylamino)-6-(methylthio)-2-pyridin-3-ylpyrimidine-5-carboxamide di-mesylate salt;
62. N-(4-Methoxyphenyl)-4-(methylamino)-6-(methylthio)-2-pyridin-3-ylpyrimidine-5-carboxamide mesylate salt;
63. N-(4-Methoxyphenyl)-4-(methylamino)-6-(methylthio)-2-pyridin-3-ylpyrimidine-5-carboxamide oxalate salt and
64. N-(4-Methoxyphenyl)-4-(methylamino)-6-(methylthio)-2-pyridin-3-ylpyrimidine-5-carboxamide bezylate salt.

Preferred salts for the list of compounds above are hydrochloride, phosphonate, mesylate, besylate, tosylate, and oxalate.

According to another embodiment of the present invention, there is provided a process for the preparation of novel pyrimidines of the formula (I) wherein all the symbols are as defined earlier.

Scheme I:

Reacting a compound of the formula (Ia) as disclosed in our US Patent 2004-259891, with substituted or unsubstituted alkylamines to produce a compound of formula (I).

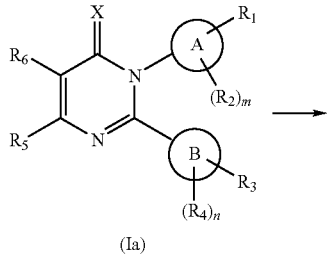

(Ia)

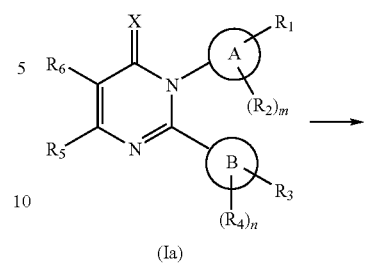

(Ia)

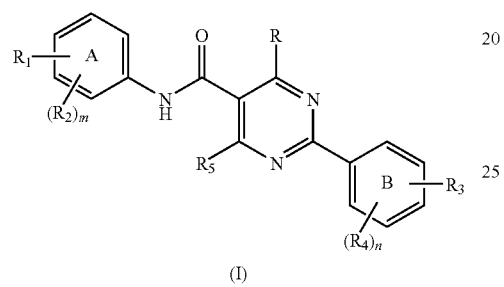

(I)

(Compound of the formula (Ia) as disclosed in our US Patent 2004-259891: wherein X represents oxygen, sulfur or NR, wherein R represents hydrogen, hydroxyl, acyl, alkyl, alkoxy, aryl, amino, hydroxylamino, alkylamino, arylamino, acylamino, alkoxyamino group; the rings represented by A and B are selected from aryl or heteroaryl; $R^1$ and $R^3$ may be same or different and independently represent hydrogen, $SR^7$, $S(O)_pR^8$; $R^2$ and $R^4$ may be same or different and independently represent hydrogen, halogen, hydroxyl, nitro, cyano, azido, nitroso, amino, formyl, alkyl, haloalkyl, acyl, alkoxy, monoalkylamino, dialkylamino, acylamino, alkoxycarbonyl, $SR^7$, $S(O)_pR^8$, alkoxyalkyl groups or carboxylic acids or its derivatives; $R^5$ and $R^6$ may be same or different and independently represent hydrogen, halogen, hydroxyl, nitro, cyano, azido, nitroso, amino, formyl, alkyl, aryl, aralkyl, haloalkyl, acyl, alkoxy, aryloxy, aralkoxy, heteroaryl, heterocyclyl, monoalkylamino, dialkylamino, acylamino, alkoxycarbonyl, $SR^7$, $S(O)_pR^8$, alkoxyalkyl groups or $COR^9$; $R^7$ represents hydrogen, alkyl or aryl; $R^8$ represents halogen, alkyl, amino, acylamino, arylamino or aryl group; $R^9$ represents hydrogen, hydroxyl, amino, halogen, alkyl, alkoxy, aryloxy, monoalkylamino, dialkylamino, acylamino, arylamino, groups; m is an integer and is in the range of 0 to 4; n is an integer and is in the range of 0 to 4; p represents an integer of 1 or 2; with a proviso that when $R^1$ represents hydrogen $R^2$ is not hydrogen.)

Scheme II: Compound of Formula (1) May Also be Prepared by Following Steps:

Step: I

Reacting a compound of formula (Ia) with a base to give the compound of formula (II), wherein all the symbols are as defined above under acidic/base catalysed conditions.

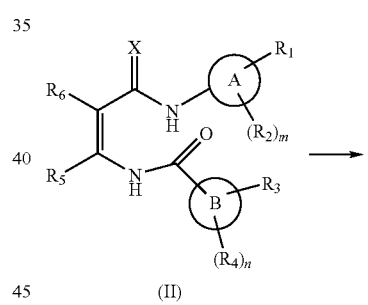

(II)

Step: II

Compound of formula (I) wherein R represents hydroxyl and all the other symbols are as defined earlier may also be prepared by cyclizing the compound of the formula (II).

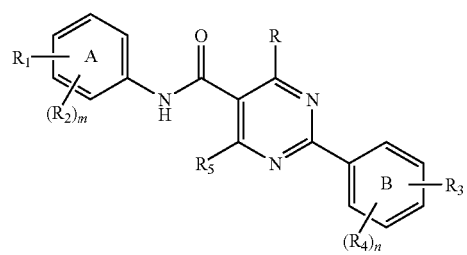

(II)

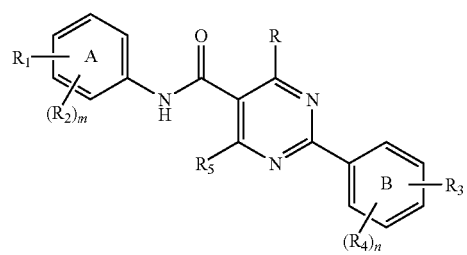

(I)

wherein R is ——OH

Step: III

Compound of formula (I) wherein R represents a halogen atom and all the other symbols are as defined earlier may also be prepared by reacting the compound of the formula (I, wherein R represents —OH) using halogenating agent.

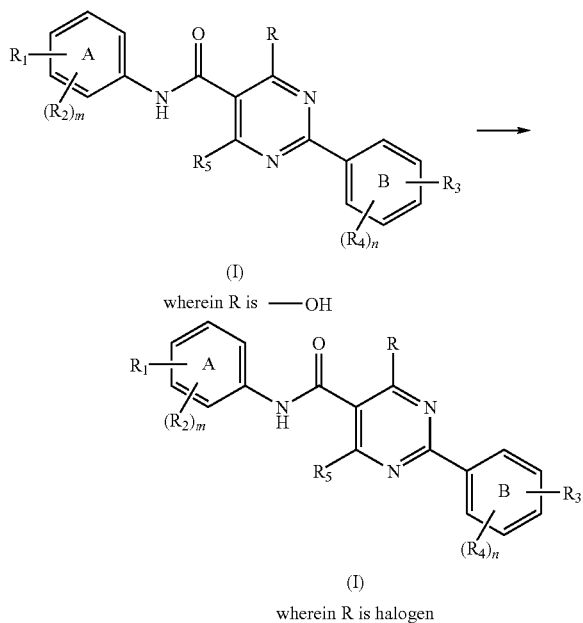

(I)
wherein R is ——OH (I)
wherein R is halogen

Step: IV

Reacting the compound of the formula (I, wherein R is halogen) to give a compound of formula (I) wherein all the other symbols are as defined earlier using suitable nucleophiles.

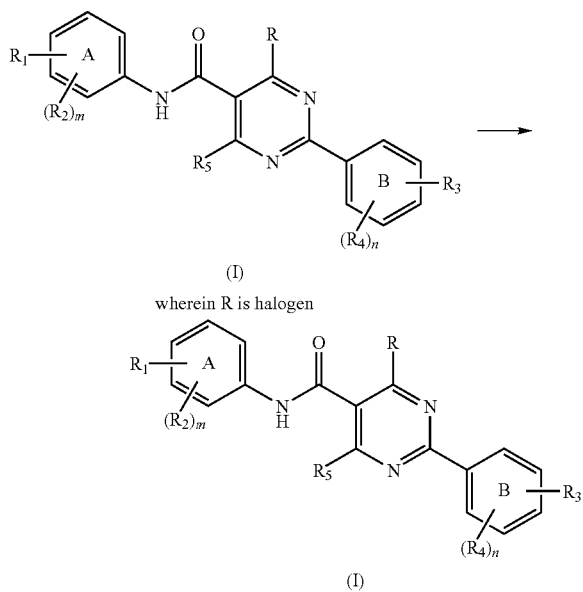

(I)
wherein R is halogen (I)

The Reactions Described in the Processes Outlined Above are Performed by Using the Methods Described Herein:

Scheme 1:

The reaction of compound of formula (Ia) with substituted or unsubstituted alkylamines may be carried out using appropriate solvents like water, toluene, xylene, THF, dioxane, chloroform, dichloromethane, dichloroethane, o-dichlorobenzene, acetone, ethyl acetate, acetonitrile, dimethylformamide, dimethylacetamide, dimethyl sulphoxide, pyridine, ethanol, methanol, isopropylalcohol, tert-butylalchol, acetic acid, propionic acid etc, a mixture thereof or by neat reactions. The condensation reaction may be carried out under acidic conditions using mineral/organic acids, or basic conditions viz. carbonates, bicarbonates, hydrides, hydroxides, alkyls and alkoxides of alkali metals and alkaline earth metals. The reaction may be carried out in presence of phase transfer catalysts viz. triethylbenzylammonium chloride, tetrabutylammonium bromide, tetrabutylammonium hydrogensulphate, tricaprylmethylammonium chloride (aliquat 336) and the like. The reaction is usually carried out under cooling to reflux conditions. The final product is purified by using chromatographic techniques or by recrystallization. The reaction may be carried out for a period in the range of 30 minutes to 20 hours.

Scheme II:

Step 1:

The conversion of formula (Ia) may be carried out in the presence of basic conditions viz. with one or more equivalents of carbonates, bicarbonates, hydrides, hydroxides, alkyls and alkoxides of alkali metals and alkaline earth metals and the like in appropriate solvents like water, ethanol, methanol, isopropylalcohol, tert-butylalchol, toluene, xylene, THF, dioxane, chloroform, dichloromethane, dichloroethane, o-dichlorobenzene, acetone, ethyl acetate, acetonitrile, dimethyl formamide, dimethyl sulphoxide, pyridine a mixture thereof or the like. The reaction can also be carried out in presence of phase transfer catalysts viz. triethylbenzylammonium chloride, tetrabutylammonium bromide, tetrabutylammonium hydrogensulphate, tricaprylmethylammonium chloride (aliquat 336) and the like. The reaction is usually carried out under cooling to reflux conditions for a period in the range of 30 minutes to 20 hours. The final product is purified by chromatographic techniques or by recrystallization.

Step 2:

The conversion of the compound of formula (II) to compound of formula (III), wherein R represents hydroxyl is carried out by using dry hydrogen chloride gas in solvents such as ethanol, methanol, dioxane, toluene, xylene, THF, dioxane, chloroform, dichloromethane, dichloroethane, o-dichlorobenzene, diphenyl ether and the like or a mixture thereof or by using reagents such as phosphorus oxychloride, thionyl chloride, phosphorus trichloride, phosphorus pentachloride, oxalyl chloride or and the like or a mixture thereof in the presence or absence of solvents such as toluene, xylene, THF, dioxane, chloroform, dichloromethane, dichloroethane, o-dichlorobenzene, diphenyl ether and the like or a mixture thereof, in presence or absence of dimethyl formamide, N,N-dimethylaniline, N,N-diethylaniline and the like. The reaction is carried out at a temperature in the range of 20° C. to reflux temperature for a period in the range of 2 to 12 hours Step 3:

The conversion of compounds of formula (III) to compound of formula (IV), wherein R represents halogen is carried out using reagents such as phosphorus oxychloride, thionyl chloride, phosphorus trichloride, phosphorus pentachloride, oxalyl chloride and the like or mixtures of the above in the presence or absence of solvents such as toluene, xylene, THF, dioxane, chloroform, dichloromethane, dichloroethane, o-dichlorobenzene, diphenyl ether and the like or a mixture thereof, in presence or absence of dimethyl formamide, N,N-dimethylaniline, N,N-diethylaniline and the like.

The reaction can be carried out at a temperature in the range of 20° C. to reflux temperatures for a period in the range of 2 to 12 hours.

Step 4:

The conversion of formula (IV) may be carried out in the presence of one or more equivalents of a metal azide such as LiN$_3$, NaN$_3$, trialkyl silylazide and the like or hydrazine hydrates or substituted hydrazines or alkylamines or aminoalkanols or heterocyclylamines or cyclic amines or benzylamines or aryl or heteroarylamines or ammonia. The reaction may be carried out in the presence of solvents such as toluene, xylene, THF, dioxane, chloroform, dichloromethane, dichloroethane, o-dichlorobenzene, acetone, ethylacetate, acetonitrile, dimethyl formamide, dimethyl sulphoxide, ethanol, methanol, isopropylalcohol, tert-butylalcohol, diphenyl ether and the like or a mixture thereof. The condensation reaction may be carried out under acidic conditions using mineral/organic acids, or basic conditions viz. carbonates, bicarbonates, hydrides, hydroxides, alkyls and alkoxides of alkali metals and alkaline earth metals. The reaction may be carried out by using phase transfer catalysts viz. triethylbenzylammonium chloride, tetrabutylammonium bromide, tetrabutylammonium hydrogensulphate, tricaprylmethylammonium chloride (aliquat 336) and the like. The reaction may be carried out at a temperature in the range of ambient temperature to reflux temperature of the solvent, preferably in the range of 80° C. to 100° C. The reaction time may range from 0.5 to 18 hours.

According to yet another embodiment of the present invention there is provided a process for the conversion of novel pyrimidines of the formula (I), wherein any of the groups R or R$_5$ or R$_1$ or R$_3$ represent SR$_6$ and wherein R$_6$ represents alkyl/aryl pyrimidines of the formula (I), wherein any of the groups R or R$_5$ or R$_1$ or R$_3$ represent S(O)$_p$R$_7$, where p represents 1 or 2 and R$_7$ represents alkyl or aryl; by using a suitable oxidizing agent. The oxidizing agent may be selected from potassium peroxymonosulfate (oxone), hydrogen peroxide, tert-butylperoxide, Jones reagent, peracid [e.g peracetic acid, perbenzoic acid, m-chloroperbenzoic acid etc], chromic acid, potassium permanganate, alkali metal periodate [e.g sodium periodate, etc], magnesium mono peroxypthalate, osmium tetroxide/N-methylmorpholine-N-oxide, sodium tungstate, and the like. The oxidation is usually carried out in a solvent which does not adversely influence the reaction such as acetic acid, dichloromethane, acetone, ethyl acetate, chloroform, water, an alcohol such as methanol, ethanol, isopropanol and the like or a mixture thereof. The reaction is usually carried out under cooling to reflux conditions.

According to yet another embodiment of the present invention there is provided a process for the conversion of novel pyrimidines of the formula (I), wherein any of the groups R or R$_5$ or R$_1$ or R$_3$ represent SR$_6$ and wherein R$_6$ represents alkyl; to novel pyrimidines of the formula (I) wherein any of the groups R or R$_5$ or R$_1$ or R$_3$ represent —SCH$_2$Cl by using sulfurylchloride under conventional conditions.

According to yet another embodiment of the present invention there is provided a process for the conversion of novel pyrimidines of the formula (I), wherein R or R$_5$ or R$_1$ or R$_3$ represent S(O)$_p$R$_7$ and wherein p is 1 or 2 and R$_7$ represents alkyl; to novel pyrimidines of the formula (I) wherein R$_1$ or R$_3$ represent S(O)$_p$R$_7$, where p is 1 or 2 and R$_7$ represents amino; by using the procedure described in the literature (Huang et. al. Tetrahedron Lett., 39, 7201, 1994).

Alternatively, a process for the preparation of novel pyrimidines of the formula (I), wherein either of R$_1$ or R$_3$ represent S(O)$_p$R$_7$ wherein R$_7$ independently represents the amino, alkylamino, hydrazine, alkylhydrazine, arylhydrazino group, p represents an integer of 1 or 2 and all the other symbols are as defined earlier, comprises of reacting the compound of formula (V) wherein either of

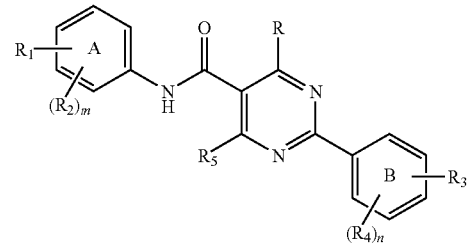

R$_1$ or R$_3$ represents hydrogen and wherein all the symbols are as defined earlier, with chlorosulfonic acid, followed by reaction with nucleophilic reagents such as ammonia, alkylamines, hydrazines, alkylhydrazines, arylhydrazines and the like.

The reaction of the compound of formula (V) with chlorosulfonic acid and ammonia may be carried out in the presence of solvents such as acetic acid, dichloromethane, acetone, THF, dioxane, ethyl acetate, chloroform, water, an alcohol and the like or a mixture thereof or in the absence of solvents. The reaction may be carried out at a temperature in the range of 0° C. to reflux temperature for a time period in the range of 2 to 24 hours.

The N-oxides of compounds according to the present invention can be prepared by methods known to those of ordinary skill in the art. For example, N-oxides can be prepared by treating an unoxidized form of the compound with an oxidizing agent (e.g., trifluoroacetic acid, per maleic acid, perbenzoic acid, peracetic acid, meta-chloroperbenzoic acid, or the like) in a suitable inert organic solvent (e.g., a halogenated hydrocarbon such as dichloromethane) at approximately 0° C. Alternatively, the N-oxides can be prepared from the N-oxide of appropriate starting material.

It is appreciated that in any of the above-mentioned reactions, any reactive group in the substrate molecule may be protected according to conventional chemical practice. Suitable protecting groups in any of the above-mentioned reactions are those used conventionally in the art. The methods of formation and removal of such protecting groups are those conventional methods appropriate to the molecule being protected. Protecting groups are removed under conditions, which will not affect the remaining portion of the molecule.

The pharmaceutically acceptable salts are prepared by reacting the compound of formula (I) with 1 to 10 equivalents of a base such as sodium hydroxide, sodium methoxide, sodium hydride, potassium t-butoxide, calcium hydroxide, magnesium hydroxide and the like, in solvents like ether, tetrahydrofuran, methanol, t-butanol, dioxane, isopropanol, ethanol etc. Mixture of solvents may be used. Organic bases such as diethanolamine, α-phenylethylamine, benzylamine, piperidine, morpholine, pyridine, hydroxyethylpyrrolidine, hydroxyethylpiperidine, choline, guanidine and the like, ammonium or substituted ammonium salts, aluminum salts. Amino acids such as glycine, alanine, cystine, cysteine, lysine, arginine, phenylalanine etc may be used for the preparation of amino acid salts. Alternatively, acid addition salts wherever applicable are prepared by treatment with acids such as hydrochloric acid, hydrobromic acid, nitric acid, sulfuric acid, phosphoric acid, p-toluenesulphonic acid, methanesulfonic acid, acetic acid, citric acid, maleic acid, salicylic acid, hydroxynaphthoic acid, ascorbic acid, palmitic acid, succinic acid, benzoic acid, benzenesulfonic acid, tartaric acid, oxalic acid and the like in solvents like ethyl acetate, ether, alcohols, acetone, tetrahydrofuran, dioxane etc. Mixture of solvents may also be used.

It should be noted that compounds of the invention may contain groups that may exist in tautomeric forms, and though one form is named, described, displayed and/or claimed herein, all the tauomeric forms are intended to be inherently included in such name, description, display and/or claim.

The stereoisomers of the compounds forming part of this invention may be prepared by using reactants in their single enantiomeric form, in the process wherever possible or by conducting the reaction in the presence of reagents or catalysts in their single enantiomer form or by resolving the mixture of stereoisomers by conventional methods. Some of the preferred methods include use of microbial resolution, resolving the diastereomeric salts formed with chiral acids such as mandelic acid, camphorsulfonic acid, tartaric acid, lactic acid, and the like wherever applicable or by using chiral bases such as brucine, cinchona alkaloids, their derivatives and the like. Commonly used methods are compiled by Jaques et al in "Enantiomers, Racemates and Resolution" (Wiley Interscience, 1981). More specifically the compounds of the formula (I) may be converted to a 1:1 mixture of diastereomeric amides by treatment with chiral amines, aminoacids, aminoalcohols derived from aminoacids; conventional reaction conditions may be employed to convert acids into amides; the diastereomers may be separated either by fractional crystallization or chromatography and the stereoisomers of the compounds of formula (I) may be prepared by hydrolysing the pure diastereomeric amides.

Prodrugs of the compounds of formula (I) are also contemplated by this invention. A prodrug is an active or inactive compound that is modified chemically through in vivo physiological action, such as hydrolysis, metabolism and the like, into a compound of this invention following administration of the prodrug to a patient. The suitability and techniques involved in making and using prodrugs are well known by those skilled in the art.

Various polymorphs of the compounds of the general formula (I), forming part of this invention may be prepared by crystallization of the compounds of formula (I) under different conditions. For example, using different commonly used solvents, or their mixtures for recrystallization; crystallizations at different temperatures; various modes of cooling, ranging from very fast to very slow cooling during crystallizations. Heating or melting the compounds followed by cooling gradually or immediately, one can also obtain polymorphs. The presence of polymorphs may be determined by solid probe NMR spectroscopy, IR spectroscopy, differential scanning calorimetry and powder X-ray diffraction or other such techniques.

The present invention also provides a pharmaceutical composition, containing one or more of the compounds of the general formula (I) as defined above, their derivatives, their analogs, their tautomeric forms, their stereoisomers, their polymorphs, their hydrates, their metabolites, their prodrugs, their pharmaceutically acceptable salts, their pharmaceutically acceptable solvates in combination with the usual pharmaceutically employed carriers, diluents and the like, useful for the treatment of inflammation, arthritis, pain, fever, psoriasis, allergic diseases, asthma, inflammatory bowel syndrome, gastro-intestinal ulcers, cardiovascular disorders including ischemic heart disease, atherosclerosis, cancer, ischemic-induced cell damage, particularly brain damage caused by stroke and other pathological disorders associated with free radicals.

The pharmaceutical composition may be in the forms normally employed, such as tablets, capsules, powders, syrups, solutions, suspensions and the like, may contain flavorants, sweeteners etc. in suitable solid or liquid carriers or diluents, or in suitable sterile media to form injectable solutions or suspensions. The compositions may be prepared by processes known in the art. The amount of the active ingredient in the composition may be less than 70% by weight. Such compositions typically contain from 1 to 25%, preferably 1 to 15% by weight of active compound, the remainder of the composition being pharmaceutically acceptable carriers, diluents, excipients or solvents.

Suitable pharmaceutically acceptable carriers include solid fillers or diluents and sterile aqueous or organic solutions. The active compound will be present in such pharmaceutical compositions in the amounts sufficient to provide the desired dosage in the range as described above. Thus, for oral administration, the compounds can be combined with a suitable solid or liquid carrier or diluent to form capsules, tablets, powders, syrups, solutions, suspensions and the like. The pharmaceutical compositions, may, if desired, contain additional components such as flavorants, sweeteners, excipients and the like. For parenteral administration, the compounds can be combined with sterile aqueous or organic media to form injectable solutions or suspensions. For example, solutions in sesame or peanut oil, aqueous propylene glycol and the like can be used, as well as aqueous solutions of water-soluble pharmaceutically-acceptable acid addition salts or alkali or alkaline earth metal salts of the compounds. The injectable solutions prepared in this manner can then be, administered intravenously, intraperitoneally, subcutaneously, or intramuscularly, with intramuscular administration being preferred in humans.

The pharmaceutical compositions of the invention are effective in lowering TNF-α and IL-6 levels, COX-2 activity without ulcers, platelet aggregation inhibition and anticancer activity as shown by tests in in-vitro as well as in animal models. The pharmaceutical compositions of the invention are thus effective for treating rheumatoid arthritis, osteoarthritis, rheumatoid spondylitis, gouty arthritis, inflammatory bowel disease, psoriasis, Crohn's disease, allergic rhinitis, ulcerative colitis, bone resorption diseases, and osteoporosis. The pharmaceutical compositions of the invention are also effective in the treatment of ischemic heart disease, ischemic-induced cell damage, ischemia reperfusion injury, atherosclerosis, brain trauma, multiple sclerosis, sepsis, septic shock, toxic shock syndrome, fever, and myalgias due to infection. The pharmaceutical compositions of the present invention are also effective in treating cancer, acute and chronic myelogenous leukemia, multiple myeloma, and pancreatic β cell destruction. Furthermore, pharmaceutical compositions of the present invention are useful for the treatment of disorders, which includes adult respiratory distress syndrome (ARDS), anaphylaxis, contact dermatitis, asthma, muscle degeneration, cachexia, type I and type II diabetes. Generally, the effective dose for treating a particular condition in a patient may be readily determined and adjusted by the physician during treatment to alleviate the symptoms or indications of the condition or disease. Generally, a daily dose of active compound in the range of about 0.01 to 1000 mg/kg of body weight is appropriate for administration to obtain effective results. The daily dose may be administered in a single dose or divided into several doses. In some cases, depending upon the individual response, it may be necessary to deviate upwards or downwards from the initially prescribed daily dose. Typical pharmaceutical preparations normally contain from about 0.2 to about 500 mg of active compound of formula I and/or its pharmaceutically active salts or solvates per dose.

While the compounds of the invention can be administered as the sole active pharmaceutical agent, they can also be used in combination with one or more compounds of the invention or other agents. When administered as a combination, the therapeutic agents can be formulated as separate compositions that are given at the same time or different times, or the therapeutic agents can be given as a single composition.

The term "therapeutically effective amount" or "effective amount" refers to that amount of a compound or mixture of compounds of Formula I that is sufficient to effect treatment, as defined below, when administered alone or in combination with other therapies to a mammal in need of such treatment. More specifically, it is that amount that is sufficient to lower the cytokines such as TNF-α, IL-1, IL-6, IL-1β, IL-8, IL-12 and cyclooxygenases such as COX-2 and COX-3 and diseases mediated by thromboxane synthase to treat autoimmune diseases, inflammation, immunological diseases, and cancer. The term "animal" as used herein is meant to include all mammals, and in particular humans. Such animals are also referred to herein as subjects or patients in need of treatment. The therapeutically effective amount will vary depending upon the subject and disease condition being treated, the weight and age of the subject, the severity of the disease condition, the particular compound of Formula I chosen, the dosing regimen to be followed, timing of administration, the manner of administration and the like, all of which can readily be determined by one of ordinary skill in the art.

The term "treatment" or "treating" means any treatment of a disease in a mammal, including:

a) Preventing the disease, that is, causing the clinical symptoms of the disease not to develop;

b) Inhibiting the disease, that is, slowing or arresting the development of clinical symptoms; and/or c) Relieving the disease, that is, causing the regression of clinical symptoms.

From the foregoing description, once skilled in the art can easily ascertain the essential characteristics of this invention, and without departing from the spirit and scope thereof, can make various changes and modifications of the invention to adapt it to various usages and conditions.

The present invention is provided by the examples given below, which are provided by the way of illustration only, and should not be considered to limit the scope of the invention. Variation and changes, which are obvious to one skilled in the art, are intended to be within the scope and nature of the invention, which are defined in the appended claims.

Preparation 1

Synthesis of N-[(1E)-2-Cyano-3-[(4-methylphenyl)amino]-1-(methylthio)-3-oxoprop-1-en-1-yl]-4-(methylthio)benzamide

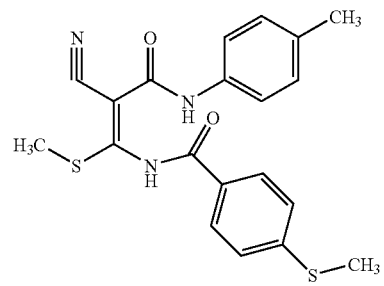

To a suspension of 5-Cyano-1-(4-methylphenyl)-4-(methylthio)-2-[4-(methylthio)phenyl]-6-oxo-1,6-dihydropyrimidine (2.5 g, 6.59 mmol) in ethanol (30 ml) was added anhydrous potassium carbonate (1.3 g, 9.4 mmol) under continuos stirring, and at an ambient temperature. The suspension was heated slowly to 60° C. under stirring for 5 hours. Subsequently the reaction mixture was filtered, and washed with water then with ethanol and dried under vacuum to yield the title compound (2.12 g, 80.8%, m.p.: 173-175° C., purity 91.6% by HPLC). $^1$H-NMR (CDCl$_3$)δ (ppm): 2.34 (s, 3H), 2.53 (s, 3H), 2.69 (s, 3H), 7.16-7.18 (d, 2H), 7.26-7.37 (m, 4H), 7.92-7.94 (d, 2H), 14.0 (s, 1H, D$_2$O exchangeable). IR (KBr) cm$^{-1}$: 3311, 2201, 1702 (—C═O). MS m/z: 398.5 (M$^+$+1).

Preparation 2

Synthesis of N-[(E)-2-Cyano-3-[(3,4-dimethylphenyl)amino]-1-(methylthio)-3-oxoprop-1-en-1-yl]-4-(methylthio)benzamide

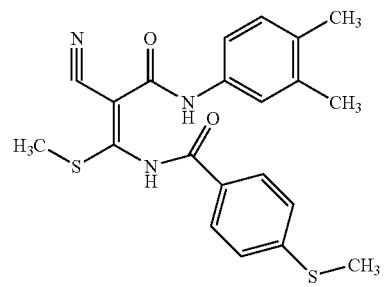

The title compound was obtained from 5-Cyano-1-(3,4-dimethylphenyl)-4-(methylthio)-2-[4-(methylthio) phenyl]-6-oxo-1,6-dihydropyrimidine (10 g, 25 mmol) by following the same procedure as described in preparation 1, 8.1 g, 77.45% yield, m.p.: 163-166° C., purity 99.7% by HPLC. $^1$H-NMR (DMSO-d$_6$) δ (ppm): 2.03 (s, 3H), 2.08 (s, 3H), 2.15 (s, 3H), 2.49(s, 3H), 6.90-6.92 (d, 2H), 6.97 (s, 1H), 7.06-7.08 (d, 2H), 8.01-8.03 (d, 2H), 11.73 (s, 1H, D$_2$O exchangeable). IR (KBr) cm$^{-1}$: 3430, 2186, and 1628 (—C═O). MS m/z: 412.1 (M$^+$+1).

EXAMPLE 1

Synthesis of 4-Hydroxy-N-(4-methylphenyl)-6-(methylthio)-2-[4-(methylthio) phenyl]pyrimidine-5-carboxamide

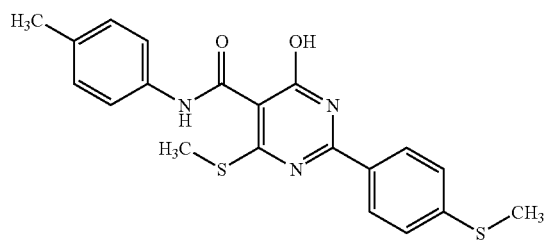

Dry HCl gas was passed through a solution of N-[(1E)-2-Cyano-3-[(4-methylphenyl)amino]-1-(methylthio)-3-oxo-prop-1-en-1-yl]-4-(methylthio)benzamide (2 g, 5 mmol, prepared according to the procedure described in preparation 1) in ethanol (50 ml) at 0° C. for 4 hours. The reaction mixture was then refluxed for 4 hours until completion; subsequently the resultant solid was filtered and washed with ethanol. The solid thus obtained was suspended in dichloromethane (50 ml), filtered, and finally dried under vacuum to yield the title compound (1.8 g, 90%, purity 99.78% by HPLC), m.p.: 302-305° C. $^1$H-NMR (CDCl$_3$) δ (ppm): 2.29 (s, 3H), 2.33 (s, 3H), 2.63 (s, 3H), 7.12-7.14 (d, 2H), 7.23-7.26 (m, 2H), 7.47-7.49 (d, 2H), 8.13-8.15 (d, 2H), 11.38 (s, 1H, D$_2$O exchangeable), 12.45 (s, 1H, D$_2$O exchangeable). IR (KBr) cm$^{-1}$: 3436, 3320, and 1646. MS m/z: 398.1(M$^+$+1).

EXAMPLE 2

Synthesis of 4-Hydroxy-N-(3,4-dimethylphenyl)-6-(methylthio)-2-[4-(methylthio) phenyl]pyrimidine-5-carboxamide

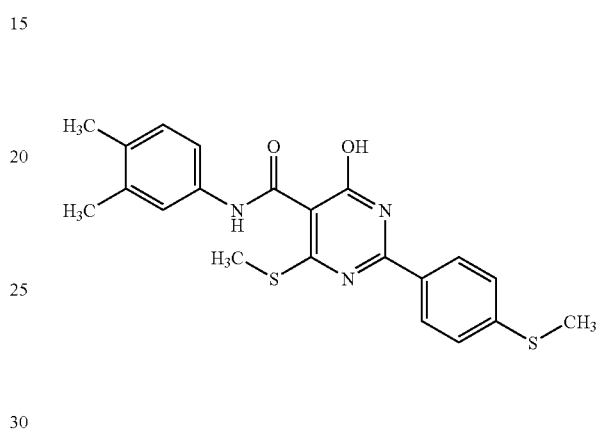

The title compound was obtained from N-[(1E)-2-Cyano-3-[(3,4-dimethylphenyl)amino]-1-(methylthio)-3-oxoprop-1-en-1-yl]-4-(methylthio) benzamide (4.4 g, 10 mmol, prepared according to the procedure described in preparation 1) by following the procedure described in example 1, 3.3 g, yield 75%, and purity 99.89% by HPLC, mp 303-305° C. $^1$H-NMR (DMSO-d$_6$) δ (ppm): 2.18-2.22 (d, 6H), 2.51-2.56 (d, 6H), 7.08-7.10 (d, 1H), 7.38-7.45 (q, 4H), 8.20-8.22 (d, 2H), 11.69 (s, 1H, D$_2$O exchangeable), 13.35 (s, 1H, D$_2$O exchangeable). IR (KBr) cm$^{-1}$: 3281, 2920, 2852 and 1650. MS m/z: 412.1 (M$^+$+1).

The Compound 3 was Prepared by the Procedure Described for Example 2.

| Exp. | Structure | Analytical data |
|---|---|---|
| 3 | (structure shown, m.p.: 316–319° C.) | Purity (HPLC): 97.32%; $^1$H-NMR (DMSO-d$_6$) δ (ppm): 2.49 (s, 3H), 2.63 (s, 3H), 7.25-7.27 (d, 2H), 7.45 (s, 2H), 7.61-7.63 (d, 2H), 8.31-8.32 (d, 2H), 11.74 (s, 1H, D$_2$O exchangeable), 12.54(s, 1H, D$_2$O exchangeable); IR (KBr) cm$^{-1}$: 3434, 2918, 1661 and 1601; MS: m/z 402.2 (M$^+$+1). |

EXAMPLE 4

Synthesis of 4-Chloro-N-(4-methylphenyl)-6-(methylthio)-2-[4-(methylthio) phenyl]pyrimidine-5-carboxamide

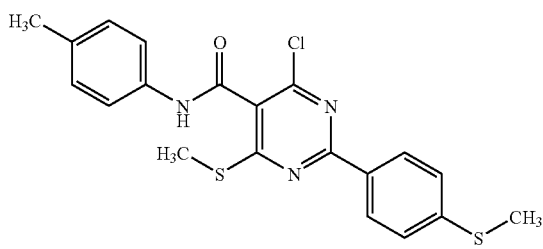

4-Hydroxy-N-(4-methylphenyl)-6-(methylthio)-2-[4-(methylthio)phenyl] pyrimidine-5-carboxamide (0.5 g, 1.25 mmol) was refluxed in phosphorus oxychloride (10 ml) for 3 hours and subsequently cooled to room temperature. The reaction mixture was poured onto ice-water mixture, neutralised with saturated sodium bicarbonate solution and the solid thus separated was extracted with ethylacetate. The organic layer was washed with water; dried over anhydrous sodium sulphate and concentrated under reduced pressure to afford the title compound, 0.3 g, yield 57%.

$^1$H-NMR (CDCl$_3$) δ (ppm): 2.35 (s, 3H), 2.55 (s, 3H), 2.69 (s, 3H), 7.19-7.21 (d, 2H), 7.3-7.32 (d, 2H), 7.51-7.53 (m, 3H, 1H D$_2$O exchangeable), 8.35-8.37 (d, 2H). IR (KBr) cm$^{-1}$: 3436, 3276, and 1648. MS m/z: 416 (M$^+$+1).

EXAMPLE 5

Synthesis of 4-(Methylamino)-N-(4-methylphenyl)-6-(methylthio)-2-[4-(methylthio)phenyl]pyrimidine-5-carboxamide

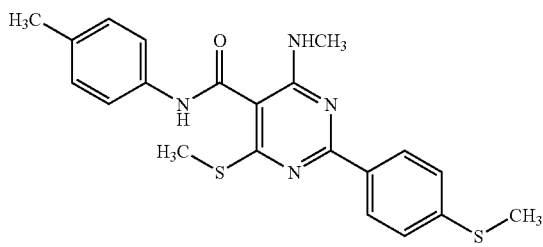

To a solution of 5-Cyano-1-(4-methylphenyl)-4-(methylthio)-2-[4-(methylthio)phenyl]-6-oxo-1,6-dihydropyrimidine (2 g, 5.3 mmol, prepared according to the procedure disclosed in our US patent 2004/0259891) in DMF was added methylamine (0.32 g, 10.5 mmol) under stirring. The solution was slowly warmed to 45° C., and maintained at this temperature for 1 hour. The completion of the reaction confirmed by TLC using ethylacetate:hexane (1:1) as a solvent system. The resulted reaction mass was poured onto ice and filtered, the crude solid thus obtained was purified by column chromatography using ethylacetate:hexane to give the title compound, 0.8 g, yield 37%, purity 99.5% by HPLC, m.p.: 228-230° C. $^1$H-NMR (CDCl$_3$) δ (ppm): 2.35 (s, 3H), 2.54 (s, 3H), 2.73 (s, 3H), 3.1-3.13 (d, 3H), 7.17-7.20 (d, 2H), 7.30-7.32 (d, 2H), 7.48-7.5 (d, 2H), 7.9 (bs, 1H), 8.35 (bs, 1H), and 8.4-8.42 (d, 2H). IR (KBr) cm$^{-1}$: 3358, 3270, and 1625. MS m/z: 411.1 (M$^+$+1).

Example 5 can be Alternatively Synthesized as Follows:

To a solution of 4-Chloro-N-(4-methylphenyl)-6-(methylthio)-2-[4-(methylthio)phenyl]pyrimidine-5-carboxamide (0.05 g, 0.12 mmol, obtained according to the procedure described in example 4) in THF (5 ml) was added 10% methylamine in THF (5 ml, prepared by purging methylamine gas into THF at 0° C. to get a 10% solution) at 0° C. under stirring. The reaction mixture was stirred at this temperature until completion (TLC) and was subsequently poured onto ice-water mixture and extracted with ethylacetate. The organic layer was dried over anhydrous sodium sulphate and distilled under vacuum to yield the title compound, 0.03 g, yield 61%. MS m/z: 411.1 (M$^+$+1).

EXAMPLE 6

Synthesis of N-(4-Methoxyphenyl)-4-(methylamino)-6-(methylthio)-2-pyridin-3-ylpyrimidine-5-carboxamide

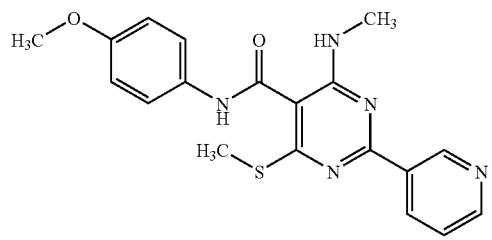

To a solution of methylamine in THF (45% solution, prepared by purging dry methylamine gas into THF at −20° C.) was added 1-(4-Methoxyphenyl)-4-(methylthio)-6-oxo-2-pyridin-3-yl-1,6-dihydropyrimidine-5-carbonitrile (1.6 g, 4.1 mmol, prepared according to the procedure disclosed in our US patent 2004-259891) under stirring at −20° C. The resultant reaction mass was stirred at the same temperature until the completion of the reaction was confirmed by TLC using ethylacetate:hexane (1:1). Subsequently the reaction mixture was poured onto ice-water mixture under vigorous stirring, until a solid separated out, which was filtered, and washed thoroughly with cold water to yield the title compound 1.47 g, yield 84.44%, purity 96.6% by HPLC, m.p.: 184-197° C. $^1$H-NMR (DMSO-d$_6$) δ (ppm): 2.72 (s, 3H), 3.11-3.13 (d, 3H), 3.8 (s, 3H), 6.92-6.94 (m, 2H), 7.37-7.41 (m, 1H), 7.51-7.53 (m, 2H), 7.90 (s, 1H, D$_2$O exchangeable), 8.37 (s, 1H, D$_2$O exchangeable), 8.68-8.70 (m, 2H), 9.65 (s, 1H). IR (KBr) cm$^{-1}$: 3285,1642. MS m/z: 382.4 (M$^+$+1).

EXAMPLE 7

Synthesis of N-(3,4-Dimethylphenyl)-4,6-bis(methylamino)-2-pyridin-3-ylpyrimidine-5-carboxamide

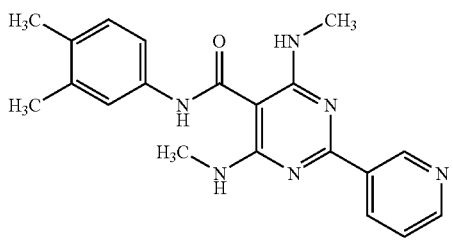

To a solution of 5-Cyano-1-(3,4-dimethylphenyl)-4-(methylthio)-6-oxo-2-pyridin-3-yl-1,6-dihydropyrimidine (0.6 g, 1.72 mmol, prepared according to the procedure disclosed in our US Patent 2004/0259891) in THF was added methylamine (0.36 g, 11.6 mmol) under stirring at an ambient temperature, and the reaction mixture was maintained at this temperature for 4 hours until completion of the reaction was confirmed by TLC using ethylacetate:hexane (1:1). The resultant reaction mass was poured onto ice and filtered. The crude solid thus obtained was purified by column chromatography using ethylacetate:hexane to give the title compound, 0.23 g, yield 38.44%, purity 94.3% by HPLC, m.p.: 285-286° C. $^1$H-NMR (CDCl$_3$) δ (ppm): 2.26-2.29 (d, 6H), 2.72 (s, 3H), 3.09-3.12 (d, 3H), 6.5 (bs, 1H, D$_2$O exchangeable), 7.13-7.15 (d, 1H), 7.26-7.39 (m, 3H, 1H, D$_2$O exchangeable), 7.88-7.93 (bs, 1H), 8.37 (bs, 1H, D$_2$O exchangeable), 8.66-8.7 (m, 2H), and 9.62-9.65 (m, 1H). IR (KBr) cm$^{-1}$: 3246, and 1641. MS m/z: 363.2 (M$^+$+1).

General Procedure:

To the suspension/solution of 1,2-Diaryl-5-cyano-4-methylthio-1,6-dihydro-pyrimidin-6-one (prepared according to the procedure disclosed in our US patent 2004-259891) in appropriate solvents like DMF, acetonitrile, ethanol, isopropanol, dioxane, THF, dichloromethane, chloroform or mixture thereof was added 1 to 30 molar quantities of methylamine/ethanolamine or substituted alkylamine under stirring at −20° C. to reflux temperature in presence or absence of a catalytic amount of anhydrous potassium carbonate. The reaction mass was stirred until completion of reaction (as confirmed by TLC). Subsequently the resultant solid thus separated was filtered, washed with water and dried to yield crude product, which was purified by column chromatography to yield the title compounds.

The Following Compounds are Prepared by the General Procedure Given Above:

| Exp. | Structure | Analytical data |
|---|---|---|
| 8 | (structure shown) m.p.: 212–216° C., | Purity (HPLC): 99.85%; $^1$H-NMR (CDCl$_3$) δ (ppm): 1.22-1.25 (t, 3H), 2.53 (s, 3H), 2.64-2.66 (q, 2H), 2.73 (s, 3H), 3.12-3.13 (d, 3H), 7.2-7.26 (d, 2H), 7.3-7.32 (d, 2H), 7.5-7.52 (d, 2H), 7.9 (bs, 1H, D$_2$O exchangeable), 8.34 (bs, 1H, D$_2$O exchangeable), 8.4-8.42 (d, 2H); IR (KBr) cm$^{-1}$: 3383, 3289 and 1625; MS m/z: 425.1 (M$^+$+1). |
| 9 | (structure shown) m.p.: 190–193° C., | Purity (HPLC): 99.2%; $^1$H-NMR (DMSO-d$_6$) δ (ppm): 2.19-2.2 (d, 6H), 2.52 (s, 3H), 2.53 (s, 3H), 2.96-2.97 (d, 3H), 6.99 (s, 1H, D$_2$O exchangeable), 7.01-7.07 (d, 1H), 7.36-7.41 (m, 3H), 7.5 (s, 1H), 8.33-8.35 (d, 2H), 10.29 (s, 1H, D$_2$O exchangeable); IR (KBr) cm$^{-1}$: 3340, 3155, 2922, 1738 and 1668; MS m/z: 425.2 (M$^+$+1). |
| 10 | (structure shown) m.p.: 205–207° C., | Purity (HPLC): 96.0%; $^1$H-NMR (DMSO-d$_6$) δ (ppm): 2.2 (s, 3H), 2.37 (s, 3H), 2.87-2.88 (d, 3H), 2.91-2.93 (d, 3H), 7.21 (s, 1H, D$_2$O exchangeable), 7.41-7.51 (m, 6H), 7.97-7.99 (d, 1H), 8.25 (s, 1H, D$_2$O exchangeable), 8.46 (s, 2H, D$_2$O exchangeable), 9.75 (bs, 1H, D$_2$O exchangeable); IR (KBr) cm$^{-1}$: 3412, 3327 and 1637; MS m/z: 441.2 (M$^+$+1). |

| Exp. | Structure | Analytical data |
|---|---|---|
| 11 | 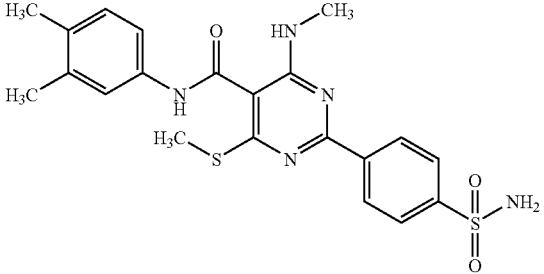<br>m.p.: 268–270° C. | Purity (HPLC): 98.9%; $^1$H--d$_6$) δ(ppm): 2.31(s, 3H), 2.45 (s, 3H), 2.59 (s, 3H), 2.96-2.97(d, 3H), 7.37-7.38 (d, 1H, D$_2$O exchangeable), 7.51 (bs, 2H, D$_2$O exchangeable), 7.52-7.53 (d, 3H), 7.76 (s, 1H), 8.41 (s, 1H), 8.42-8.43 (d, 2H), 10.61 (bs, 1H, D$_2$O exchangeable); IR (KBr) cm$^{-1}$: 3406, 3313 and 1646; MS m/z: 458.2 (M$^+$+1). |
| 12 | 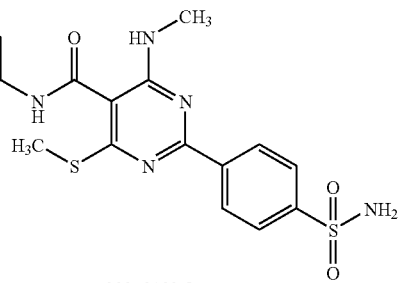<br>m.p.: 208–210° C. | Purity (HPLC): 98.4%; $^1$H-NMR (DMSO d$_6$) δ (ppm): 2.51 (s, 3H), 2.55 (s, 3H), d$_6$) δ(ppm): 2.51 (s, 3H), 2.55 (s, 3H), 2.96-2.97 (d, 3H), 7.11-7.12 (m, 1H, D$_2$O exchangeable), 7.33-7.35 (d, 1H), 7.38 (bs, 2H, D$_2$O exchangeable), 7.5-7.53 (m, 3H), 7.78-7.81 (m, 1H), 8.31-8.32 (d, 1H), 8.41-8.43 (d, 2H),10.71 (bs, 1H, D$_2$O exchangeable); IR (KBr) cm$^{-1}$: 3409, 3318 and 1646; MS m/z: 444.1 (M$^+$+1). |
| 13 | 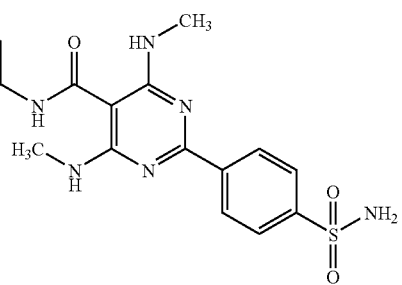<br>m.p.: > 285° C. | Purity (HPLC): 93.5%; $^1$H-NMR (DMSO-d$_6$) δ (ppm): 2.31(s, 3H), 2.54 (s, 3H), 3.3-3.34 (d, 3H), 7.31-7.33 (m, 3H, 2H, D$_2$O exchangeable), 7.56-7.6 (m, 3H), 7.74-7.76 (m, 4H, 1H, D$_2$O exchangeable), 8.25 (m, 1H), 14.5 (bs, 1H, D$_2$O exchangeable); IR (KBr) cm$^{-1}$: 3381, 3313, 3233 and 1656; MS m/z: 427.2 (M$^+$+1). |
| 14 | 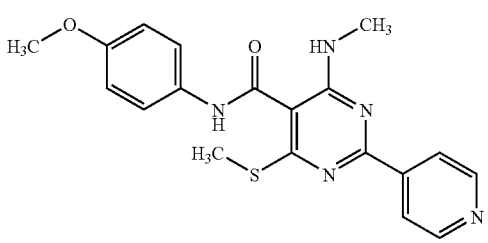<br>m.p.: 225–226° C. | Purity (HPLC): 96.6%; $^1$H-NMR (DMSO-d$_6$) δ (ppm): 2.6 (s, 3H), 2.97-2.98 (d, 3H), 3.73-3.74 (d, 3H), 6.92-6.94 (m, 2H), 7.18-7.19 (m, 1H, D$_2$O exchangeable), 7.61-7.63 (m, 2H), 7.61-7.63 (m, 3H), 8.26-8.28 (d, 2H), 8.75-8.76 (d, 2H), 10.42 (s, 1H D$_2$O exchangeable); IR (KBr) cm$^{-1}$: 3383, 3334 and 1676; MS m/z: 382.1 (M$^+$+1). |
| 15 | 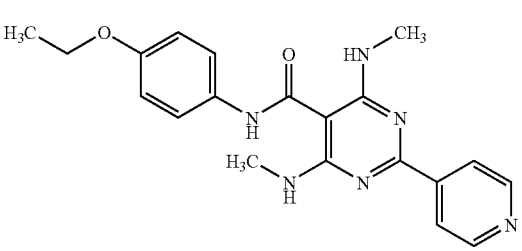<br>m.p.: 235–238° C. | Purity (HPLC): 94.0%; $^1$H-NMR (CDCl$_3$) δ (ppm): 1.12-1.14 (t, 3H), 3.02-3.04 (d, 3H), 3.29(s, 3H), 4.0-4.05(q, 2H), 6.23 (bs, 1H), 6.86-6.88 (m, 2H), 7.43-7.44 (d, 2H), 7.53-7.55 (d, 2H), 8.8-8.82 (d, 2H), 10.63 (bs, 1H), 13.92 (s, 1H); IR (KBr) cm$^{-1}$: 3385, 3139 and 1640; MS m/z: 379.3 (M$^+$+1). |

| Exp. | Structure | Analytical data |
|---|---|---|
| 16 | (structure) m.p.: decomposed at 230° C. | Purity (HPLC): 97.5%; $^1$H-NMR (DMSO-d$_6$) δ (ppm): 1.2-1.23 (t, 3H), 2.34 (s, 3H), 2.93-2.98 (q, 2H), 3.36 (s, 3H), 7.4-7.42 (m, 4H, 3H are D$_2$O exchangeable), 7.54-7.61(m, 3H), 7.71-7.72 (m, 2H), 7.79-7.82 (m, 1H), 8.19 (s, 1H); IR (KBr) cm$^{-1}$: 3380, 3267 and 1656; MS m/z: 441.2 (M$^+$+1). |
| 17 | (structure) m.p.: 226–230° C. | Purity (HPLC): 99.7%; $^1$H-NMR (DMSO-d$_6$) δ (ppm) 1.19-1.22 (t, 3H), 2.68 (s, 3H), 2.93-2.97 (m, 5H), 7.12 (bs, 1H, D$_2$O exchangeable), 7.38-7.52 (m, 4H), 7.84 (d, 1H), 8.3 (bs, 1H), 8.4-8.42 (d, 2H), 10.73 (bs, 1H, D$_2$O exchangeable); IR (KBr) cm$^{-1}$: 3406, 3373 and 1633; MS m/z: 458.2(M$^+$+1). |
| 18 | (structure) m.p.: 247–249° C. | Purity (HPLC): 99.80%; $^1$H-NMR (CDCl$_3$) δ (ppm): 2.60 (s, 3H), 2.97-2.98 (d, 3H), 7.18-7.25 (m, 3H, 1H, D$_2$O exchangeable), 7.71-7.74 (m, 2H), 8.26-8.28 (d, 2H), 8.75-8.76 (d, 2H), 10.63 (s, 1H, D$_2$O exchangeable); IR (KBr) cm$^{-1}$: 3399, 3331 and 1669; MS m/z: 370.1 (M$^+$+1). |
| 19 | (structure) m.p.: 247–249° C. | Purity (HPLC): 98.0%; $^1$H-NMR (CDCl$_3$) δ (ppm): 2.74-2.77 (d, 6H), 3.13-3.14 (d, 3H), 3.82(s, 3H), 6.92-6.94 (d, 2H), 7.51-7.54 (d, 2H), 7.72-7.74 (d, 2H), 7.91 (s, 1H), 8.35 (s, 1H, D$_2$O exchangeable), 8.61-8.63 (d, 2H); IR (KBr) cm$^{-1}$: 3337, 3224, 3114 and 1652; MS m/z: 443.1 (M$^+$+1). |
| 20 | (structure) m.p.: 214–217° C. | Purity (HPLC): 98.7%; $^1$H-NMR (CDCl$_3$) δ (ppm): 2.54 (s, 3H), 2.73 (s, 3H), 3.11-3.13 (d, 3H), 3.82 (s, 3H), 6.91-6.93 (d, 2H), 7.3-7.32 (t, 2H), 7.5-7.52 (d, 2H), 7.9 (s, 1H, D$_2$O exchangeable), 8.3 (s, 1H, D$_2$O exchangeable), 8.4-8.42 (d, 2H); IR (KBr) cm$^{-1}$: 3364, 3289, 2928 and 1618; MS m/z: 427.1 (M$^+$+1). |

| Exp. | Structure | Analytical data |
| --- | --- | --- |
| 21 | m.p.: 212–218° C. | Purity (HPLC): 98.7%; $^1$H-NMR (CDCl$_3$) δ (ppm): 1.22-1.26 (t, 3H), 2.62-2.68 (q, 2H), 2.74 (s, 3H), 3.13-3.14 (d, 3H), 7.21-7.26 (t, 2H), 7.51-7.53 (d, 2H), 7.89 (s, 1H, D$_2$O exchangeable), 8.28-8.29 (d, 2H), 8.37 (s, 1H, D$_2$O exchangeable), 8.74-8.75 (d, 2H); IR (KBr) cm$^{-1}$: 3300, 3235, 2925 and 1651; MS m/z: 380.1 (M$^+$+1). |
| 22 | m.p.: 140–150° C. | Purity (HPLC): 97.8%; $^1$H-NMR (CDCl$_3$) δ (ppm): 1.22-1.26 (t, 3H), 2.62-2.68 (q, 2H), 2.72 (s, 3H), 3.11-3.13 (d, 3H), 7.21-7.26 (t, 2H), 7.37-7.4 (t, 1H), 7.51-7.53 (d, 2H), 7.9 (s, 1H, D$_2$O exchangeable), 8.41 (s, 1H, D$_2$O exchangeable), 8.68-8.7 (q, 2H), 9.65 (s, 1H); IR (KBr) cm$^{-1}$: 3360, 3281, 2965, 2925, 2361, 1624 and 1520; MS m/z:380.0 (M$^+$+1). |
| 23 | m.p.: 195–200° C. | Purity (HPLC): 97.9%; $^1$H-NMR (DMSO-d$_6$) δ (ppm): 2.6 (s, 3H), 3.5 (d, 4H), 3.7 (s, 3H), 4.7 (s, 1H, D$_2$O exchangeable), 6.92-6.94 (d, 2H), 7.5 (s, 1H, D$_2$O exchangeable), 7.55-7.63 (m, 3H), 8.65-8.72 (m, 2H), 9.52-9.53 (d, 1H), 10.38 (s, 1H, D$_2$O exchangeable); IR (KBr) cm$^{-1}$: 3342, 2934 and 1663; MS m/z: 412 (M$^+$+1). |
| 24 | m.p.: 215–220° C. | Purity (HPLC): 99.6%; $^1$H-(CDCl$_3$) δ (ppm): 2.35 (s, 3H), 2.74 (s, 3H), 3.13-3.14 (d, 3H), 7.18-7.21 (d, 2H), 7.48-7.5 (d, 2H), 7.89 (s, 1H, D$_2$O exchangeable), 8.28-8.29 (d, 2H), 8.36 (s, 1H, D$_2$O exchangeable), 8.74-8.75 (d, 2H); IR (KBr) cm$^{-1}$: 3345, 2923, 2362, 1667 and 1596; MS m/z: 366.1 (M$^+$+1). |
| 25 | m.p.: 200–210° C. | Purity (HPLC): 99.6%; $^1$H-(CDCl$_3$) δ (ppm): 2.25 (s, 3H), 2.29 (s, 3H), 3.12-3.13 (d, 3H), 7.13-7.15 (d, 1H), 7.33-7.39 (q, 2H), 7.9 (s, 1H, D$_2$O exchangeable), 8.26-8.28 (d, 2H), 8.36 (s, 1H, D$_2$O exchangeable), 8.73-8.74 (d, 2H); IR (KBr) cm$^{-1}$: 3265, 2930, 2358, 1626 and 1525; MS m/z: 380.0 (M$^+$+1). |

| Exp. | Structure | Analytical data |
|---|---|---|
| 26 | (3,4-dimethylphenyl)-NHC(O)-[4-(methylamino)-6-(methylamino)-2-(pyridin-4-yl)pyrimidin-5-yl]carboxamide<br>m.p.: 235–240° C. | Purity (HPLC): 96.6%; ¹H-(CDCl₃) δ (ppm): 2.25 (s, 3H), 2.28 (s, 3H), 3.11-3.12 (d, 6H), 6.52-6.53 (d, 2H, D₂O exchangeable), 7.11-7.13 (d, 1H), 7.21-7.21 (d, 1H), 7.26-7.28 (d, 1H), 7.81 (s, 1H, D₂O exchangeable), 8.28-8.29 (d, 2H), 8.71-8.73 (d, 2H); IR (KBr) cm⁻¹: 3331, 2921 and 1632; MS m/z: 363.0 (M⁺+1). |
| 27 | (4-methylphenyl)-NHC(O)-[4-(methylamino)-6-(methylamino)-2-(pyridin-4-yl)pyrimidin-5-yl]carboxamide<br>m.p.: 220–225° C. | Purity (HPLC): 98.5%; ¹H-NMR (CDCl₃) δ (ppm): 2.34 (s, 3H), 3.11-3.12 (d, 6H), 6.51-6.52 (d, 2H, D₂O exchangeable), 7.17-7.19 (d, 2H), 7.37-7.39 (t, 2H), 7.87 (s, 1H, D₂O exchangeable), 8.27-8.28 (t, 2H), 8.71-8.72 (d, 2H); IR (KBr) cm⁻¹: 3331, 2923, 2362 and 1636; MS m/z: 349.2 (M⁺+1). |
| 28 | (4-methoxyphenyl)-NHC(O)-[4-(methylamino)-6-(methylamino)-2-(pyridin-3-yl)pyrimidin-5-yl]carboxamide<br>m.p.: 214–216° C. | Purity (HPLC): 95.7%; ¹H-NMR (CDCl₃) δ (ppm): 3.1-3.12 (d, 6H), 3.82 (s, 3H), 6.53-6.54 (d, 2H, D₂O exchangeable), 6.90-6.93 (q, 2H), 7.35-7.43 (q, 3H), 7.9 (s, 1H, D₂O exchangeable), 8.66-8.7 (q, 2H), 9.63 (s, 1H); IR (KBr) cm⁻¹: 3398, 3361, 1630 and 1594; MS m/z: 365.0 (M⁺+1). |
| 29 | (4-fluorophenyl)-NHC(O)-[4-(2-hydroxyethylamino)-6-(methylthio)-2-(pyridin-4-yl)pyrimidin-5-yl]carboxamide | Purity (HPLC): 95.3%; ¹H-NMR (DMSO-d₆) δ (ppm): 2.61 (s, 3H), 3.58 (s, 4H), 4.77 (s, 1H, D₂O exchangeable), 7.18-7.23 (t, 3H & 1H is D₂O exchangeable), 7.7-7.74 (q, 2H), 8.24-8.26 (q, 2H), 8.75-8.77 (q, 2H), 10.6 (s, 1H, D₂O exchangeable); MS m/z: 400.0 (M⁺+1). |
| 30 | (4-methoxyphenyl)-NHC(O)-[4-(2-hydroxyethylamino)-6-(methylthio)-2-(4-(methylthio)phenyl)pyrimidin-5-yl]carboxamide | Purity (HPLC): 93.2%; ¹H-NMR (DMSO-d₆) δ (ppm): 2.5 (s, 3H), 2.58 (s, 3H), 3.57-3.59 (d, 4H), 3.74 (s, 3H), 4.77 (s, 1H, D₂O exchangeable), 6.91-6.93 (d, 1H, D₂O exchangeable), 6.91-6.93 (d, 2H), 7.0 (s, 1H, D₂O exchangeable), 7.36-7.38 (d, 2H), 7.6-7.62 (d, 2H), 8.31-8.33 (d, 2H), 10.31 (s, 1H, D₂O exchangeable); MS m/z:457.9 (M⁺+1). |
| 31 | (4-ethylphenyl)-NHC(O)-[4-(2-hydroxyethylamino)-6-(methylthio)-2-(pyridin-4-yl)pyrimidin-5-yl]carboxamide | Purity (HPLC): 90.5%; ¹H-NMR (DMSO-d₆) δ (ppm): 1.15-1.18 (t, 3H), 2.55-2.67 (m, 5H), 3.58-3.59 (m, 4H), 4.76-4.78 (t, 1H, D₂O exchangeable), 7.14-7.2 (m, 3H & 1H is D₂O exchangeable), 7.59-7.61 (d, 2H), 8.24-8.26 (q, 2H), 8.75-8.77 (q, 2H), 10.45 (s, 1H, D₂O exchangeable); MS m/z: 410.1 (M⁺+1). |

| Exp. | Structure | Analytical data |
| --- | --- | --- |
| 32 | [Structure with 3,4-dimethylphenyl carboxamide, 4-(hydroxyethylamino)pyrimidine, methylthio, and 4-(methylthio)phenyl substituents] | Purity (HPLC): 96.8%; $^1$H-NMR (DMSO-d$_6$) δ (ppm): 2.19-2.21 (d, 6H), 2.54 (s, 3H), 2.58 (s, 3H), 3.57 (s, 4H), 4.75-4.78 (t, 1H, D$_2$O exchangeable), 6.99 (s, 1H, D$_2$O exchangeable), 7.08-7.1 (d, 1H), 7.36-7.4 (t, 3H), 7.5 (s, 1H), 8.31-8.33 (d, 2H), 10.27 (s, 1H, D$_2$O exchangeable); MS m/z: 455.1 (M$^+$+1). |
| 33 | [Structure with 4-isopropylphenyl carboxamide, 4-(methylamino)pyrimidine, methylthio, and pyridin-3-yl substituents] m.p.: 186–187° C. | Purity (HPLC): 97.8%; $^1$H-NMR (CDCl$_3$) δ (ppm): 1.25-1.26 (d, 6H), 2.73 (s, 3H), 2.9-2.93 (m, 1H), 3.12-3.13 (d, 3H), 7.24-7.39 (m, 2H), 7.38-7.41 (m, 1H), 7.51-7.53 (q, 2H), 7.9 (s, 1H, D$_2$O exchangeable), 8.36 (s, 1H), 8.69-8.72 (q, 2H), 9.67 (s, 1H); IR (KBr) cm$^{-1}$: 3421, 2954, 1656 and 1586; MS m/z: 394.1 (M$^+$+1). |
| 34 | [Structure with 4-isopropylphenyl carboxamide, 4-(methylamino)pyrimidine, methylthio, and pyridin-4-yl substituents] m.p.: 196–198° C. | Purity (HPLC): 98.3%; $^1$H-NMR (CDCl$_3$) δ (ppm): 1.25-1.28 (d, 6H), 2.74 (s, 3H), 2.88-2.95 (m, 1H), 3.1-3.14 (d, 3H), 7.24-7.25 (d, 1H), 7.26-7.27 (d, 1H), 7.51-7.54 (q, 2H), 7.89-7.9 (d, 1H, D$_2$O exchangeable), 8.28-8.3 (t, 2H), 8.34 (s, 1H, D$_2$O exchangeable), 8.74-8.76 (d, 2H); IR (KBr) cm$^{-1}$: 3391, 3282, 2921 and 1624; MS m/z: 394.1 (M$^+$+1). |
| 35 | [Structure with 4-methylphenyl carboxamide, 4-(hydroxyethylamino)pyrimidine, methylthio, and pyridin-4-yl substituents] m.p.: 215–218° C. | Purity (HPLC): 93.7%; $^1$H-NMR (CDCl$_3$) δ (ppm): 2.36 (s, 3H), 2.74 (s, 3H), 3.79-3.83 (t, 2H), 3.88-3.91 (t, 2H), 7.19-7.21 (d, 2H), 7.48-7.5 (d, 2H), 8.22-8.25 (t, 3H & 1H is D$_2$O exchangeable), 8.33 (s, 1H, D$_2$O exchangeable), 8.75-8.76 (d, 2H); IR (KBr) cm$^{-1}$: 3329, 3274, 2854 and 1645; MS m/z: 396.1 (M$^+$+1). |
| 36 | [Structure with 4-butylphenyl carboxamide, 4-(methylamino)pyrimidine, methylthio, and 4-(methylthio)phenyl substituents] m.p.: 179–180° C. | Purity (HPLC): 99.6%; $^1$H-NMR (CDCl$_3$) δ (ppm): 0.91-0.94 (t, 3H), 1.34-1.38 (t, 2H), 1.57-1.61 (t, 2H), 2.54 (s, 3H), 2.58-2.62 (t, 2H), 2.73 (s, 3H), 3.11-3.13 (d, 3H), 7.18-7.2 (d, 2H), 7.30-7.32 (d, 2H), 7.49-7.51 (d, 2H), 7.9 (s, 1H, D$_2$O exchangeable), 8.33 (s, 1H, D$_2$O exchangeable), 8.39-8.42 (d, 2H); IR (KBr) cm$^{-1}$: 3377, 3276, 2922 and 1625; MS m/z: 453.1 (M$^+$+1). |

| Exp. | Structure | Analytical data |
|---|---|---|
| 37 | (structure; m.p.: 210–212° C.) | Purity (HPLC): 96.8%; $^1$H-NMR (DMSO-d$_6$) δ (ppm): 2.19-2.21 (d, 6H), 2.60 (s, 3H), 3.58 (m, 4H), 4.78 (s, 1H, D$_2$O exchangeable), 7.09-7.13 (m, 2H, & 1H is D$_2$O exchangeable), 7.39-7.41 (d, 1H), 7.5 (s, 1H), 8.24-8.26 (d, 2H), 8.75-8.76 (d, 2H), 10.36 (s, 1H, D$_2$O exchangeable); IR (KBr) cm$^{-1}$: 3430, 2922, 1639 and 1582; MS m/z:410.1 (M$^+$+1). |
| 38 | (structure; m.p.: 232–235° C.) | Purity (HPLC): 94.2%; IR (KBr) cm$^{-1}$: 3377, 3282, 2919 and 1618; MS m/z: 443.1 (M$^+$+1). |
| 39 | (structure; m.p.: 207–211° C.) | Purity (HPLC): 96.2%; $^1$H-NMR (CDCl$_3$) δ (ppm): 2.32-2.33 (d, 6H), 2.54 (s, 3H), 2.73 (s, 3H), 3.11-3.12 (d, 3H), 7.06 (s, 2H), 7.30-7.32 (d, 2H), 7.62-7.64 (d, 1H, D$_2$O exchangeable), 7.98 (s, 1H), 8.24 (s, 1H), 8.4-8.42 (d, 2H & 1H is D$_2$O exchangeable); IR (KBr) cm$^{-1}$: 3358, 3229, 2916 and 1622; MS m/z: 425.1 (M$^+$+1). |
| 40 | (structure) | Purity (HPLC): 93.6%; $^1$H-NMR (CDCl$_3$) δ (ppm): 1.40-1.43 (t, 3H), 2.54 (s, 3H), 2.73 (s, 3H), 3.11-3.12 (d, 3H), 4.03-4.05 (d, 2H), 6.9-6.92 (d, 2H), 7.30-7.32 (d, 2H), 7.48-7.51 (d, 2H), 7.9 (s, 1H, D$_2$O exchangeable), 8.29 (s, 1H), 8.39-8.42 (d, 2H & 1H is D$_2$O exchangeable); MS m/z: 441.1 (M$^+$+1). |
| 41 | (structure; m.p.: 232–234° C.) | Purity (HPLC): 98.3%; $^1$H-NMR (CDCl$_3$) δ (ppm): 2.26 (s, 3H), 2.29 (s, 3H), 2.55 (s, 3H), 2.69 (s, 3H), 7.13-7.15 (d, 1H), 7.3-7.32 (m, 3H), 7.461-7.465 (d, 2H), 8.35-8.37 (d, 2H & 1H is D$_2$O exchangeable); IR (KBr) cm$^{-1}$: 3436, 3234, 2920 and 1642; MS m/z: 430.0 (M$^+$+1). |

| Exp. | Structure | Analytical data |
|---|---|---|
| 42 | 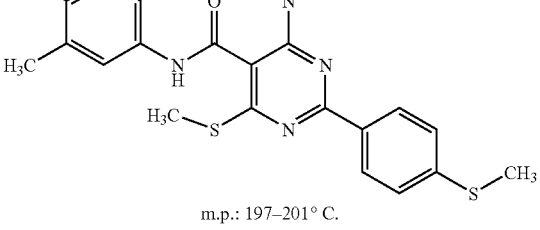<br>m.p.: 197–201° C. | Purity (HPLC): 96%; $^1$H-NMR (CDCl$_3$) δ (ppm): 2.24-2.28 (d, 6H), 2.53-2.54 (d, 4H), 2.62 (s, 3H), 2.89 (s, 3H), 3.61-3.63 (m, 4H), 7.1-7.12 (d, 1H), 7.31-7.32 (m, 3H), 7.482-7.487 (d, 1H), 7.98 (s, 1H, D$_2$O exchangeable), 8.35-8.38 (m, 2H); IR (KBr) cm$^{-1}$: 3328, 2920, 1643 and 1526; MS m/z: 480.1 (M$^+$+1). |
| 43 | 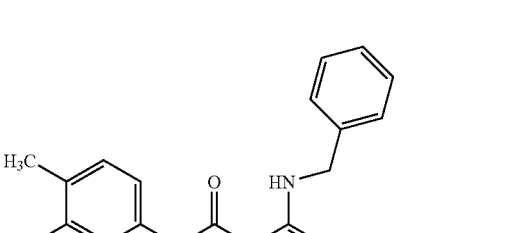<br>m.p.: 168–172° C. | Purity (HPLC): 98.5%; $^1$H-NMR (CDCl$_3$) δ (ppm): 2.24-2.27 (d, 6H), 2.53 (s, 3H), 2.73 (s, 3H), 4.82-4.84 (d, 2H), 7.11-7.13 (d, 1H), 7.24-7.3 (t, 1H, D$_2$O exchangeable), 7.31-7.33 (m, 5H), 7.37-7.39 (m, 3H), 8.28 (s, 1H, D$_2$O exchangeable), 8.35-8.37 (d, 3H); IR (KBr) cm$^{-1}$: 3368, 2922, 1623 and 1574; MS m/z: 501.1 (M$^+$+1). |
| 44 | 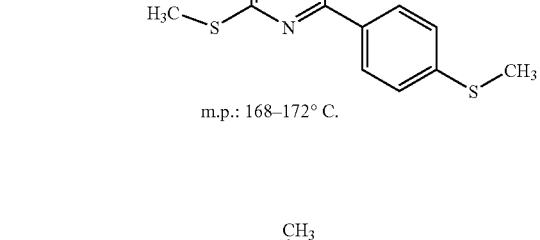<br>m.p.: 213–217° C. | Purity (HPLC): 96.7%; $^1$H-NMR (CDCl$_3$) δ (ppm): 2.24 (s, 3H), 2.28-2.29 (d, 6H), 2.47-2.49 (m, 4H), 2.53-2.54 (d, 3H), 2.62 (s, 3H), 3.67-3.69 (m, 4H), 7.1-7.12 (d, 1H), 7.31-7.32 (d, 3H), 7.47-7.48 (d, 1H), 7.95 (s, 1H, D$_2$O exchangeable), 8.35-8.37 (t, 2H); IR (KBr) cm$^{-1}$: 3435, 2919, 1633 and 1513; MS m/z: 494.1 (M$^+$+1). |
| 45 | 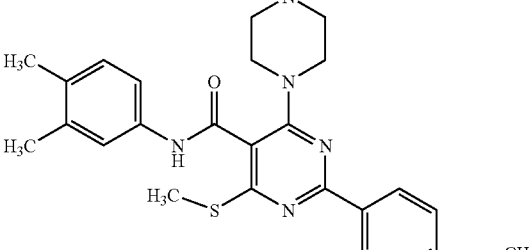<br>m.p.: 238–243° C. | Purity (HPLC): 99.3%; $^1$H-NMR (DMSO-d$_6$) δ (ppm): 2.46 (s, 3H), 2.58 (s, 3H), 2.95-2.96 (d, 3H), 7.08-7.1 (d, 1H, D$_2$O exchangeable), 7.26-7.28 (d, 2H), 7.31-7.36 (q, 2H), 7.65-7.67 (d, 2H), 8.44-8.48 (q, 2H), 10.5 (s, 1H, D$_2$O exchangeable); IR (KBr) cm$^{-1}$: 3368, 2921, 1625 and 1496; MS m/z: 415.0 (M$^+$+1). |

| Exp. | Structure | Analytical data |
|---|---|---|
| 46 | 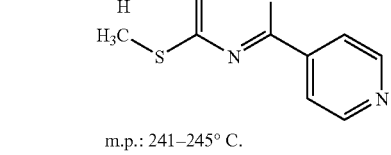<br>m.p.: 241–245° C. | Purity (HPLC): 98.8%; $^1$H-NMR (DMSO-$d_6$) δ (ppm): 2.61 (s, 3H), 3.58 (s, 4H), 4.76-4.78 (t, 1H, $D_2O$ exchangeable), 7.24 (s, 1H, $D_2O$ exchangeable), 7.54-7.56 (d, 2H), 7.66-7.68 (d, 2H), 8.24-8.26 (t, 2H), 8.75-8.77 (d, 2H), 10.68 (s, 1H, $D_2O$ exchangeable); IR (KBr) cm$^{-1}$: 3435, 2925, 1651 and 1583; MS m/z: 461.6 (M$^+$+1). |
| 47 | 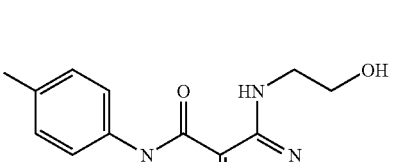<br>m.p.: 237–240° C. | Purity (HPLC): 100%; $^1$H-NMR (DMSO-$d_6$) δ (ppm): 2.61 (s, 3H), 3.58 (s, 4H), 4.76-4.77 (t, 1H, $D_2O$ exchangeable), 7.24 (s, 1H, $D_2O$ exchangeable), 7.41-7.43 (d, 2H), 7.72-7.74 (d, 2H), 8.24-8.26 (t, 2H), 8.75-8.77 (t, 2H), 10.68 (s, 1H, $D_2O$ exchangeable); IR (KBr) cm$^{-1}$: 3428, 2926, 1651 and 1531; MS m/z: 416.3 (M$^+$+1). |
| 48 | 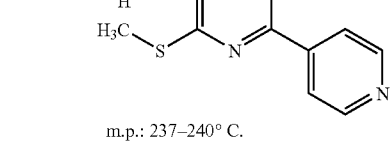<br>m.p.: 190–193° C. | Purity (HPLC): 95%; $^1$H-NMR (DMSO-$d_6$) δ (ppm): 2.18-2.22 (d, 6H), 2.54 (s, 3H), 2.57 (s, 3H), 4.53 (s, 2H, $D_2O$ exchangeable), 7.06-7.08 (d, 1H), 7.35-7.37 (m, 3H), 7.47 (s, 1H), 8.24 (s, 1H, $D_2O$ exchangeable), 8.37-8.39 (m, 2H), 10.19 (s, 1H, $D_2O$ exchangeable); IR (KBr) cm$^{-1}$: 3429, 3251, 2920, 1639 and 1622; MS m/z: 426.2 (M$^+$+1). |
| 49 | 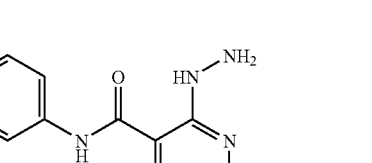<br>m.p.: 192–196° C. | Purity (HPLC): 92.2%; $^1$H-NMR (CDCl$_3$) δ (ppm): 2.33-2.34 (d, 6H), 2.75 (s, 3H), 3.8-3.82 (m, 2H), 3.87-3.9 (m, 2H), 7.06-7.08 (d, 2H), 7.62-7.64 (d, 1H, $D_2O$ exchangeable), 8.22-8.23 (d, 3H), 8.39 (s, 1H, $D_2O$ exchangeable), 8.76-8.77 (d, 2H); IR (KBr) cm$^{-1}$: 3429, 3313, 2923, 1642 and 1527; MS m/z: 409.9 (M$^+$+1). |
| 50 | 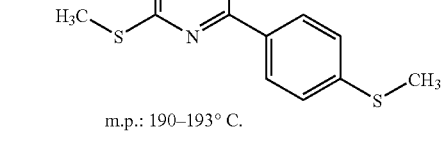<br>m.p.: 204–207° C. | Purity (HPLC): 97.3%; $^1$H-NMR (CDCl$_3$) δ (ppm): 2.53 (s, 3H), 2.75 (s, 3H), 3.32-3.35 (t, 1H, $D_2O$ exchangeable), 3.79-3.82 (m, 2H), 3.87-3.9 (m, 2H), 7.12-7.18 (m, 2H), 7.29-7.31 (d, 2H), 7.69-7.74 (m, 1H, $D_2O$ exchangeable), 8.31-8.35 (t, 3H), 8.45 (s, 1H, $D_2O$ exchangeable); IR (KBr) cm$^{-1}$: 3401, 3266, 1618 and 1515; MS m/z: 463.4 (M$^+$+1). |

| Exp. | Structure | Analytical data |
|---|---|---|
| 51 | 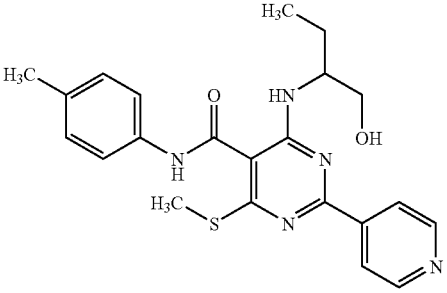<br>m.p.: 247–251° C. | Purity (HPLC): 92.6%; $^1$H-NMR (CDCl$_3$) δ (ppm): 0.70-0.74 (t, 3H), 1.72-1.74 (m, 1H), 2.08-2.15 (m, 1H), 2.25 (s, 3H), 2.33 (s, 3H), 3.69-3.71 (d, 1H, D$_2$O exchangeable), 3.77-3.8 (t, 1H, D$_2$O exchangeable), 4.21-4.23 (m, 1H), 4.48-4.49 (m, 1H), 7.13-7.15 (d, 2H), 7.53-7.55 (m, 2H), 7.58-7.62 (m, 2H), 8.8-8.84 (q, 2H), 11.65(s, 1H, D$_2$O exchangeable);IR (KBr) cm$^{-1}$: 3437, 2923, 1668 and 1527; MS m/z: 425.2 (M$^+$+2). |
| 52 | 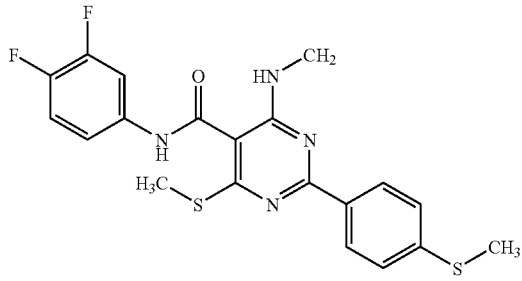<br>m.p.: 212–214° C. | Purity (HPLC): 93.4%; $^1$H-NMR (DMSO-d$_6$) δ (ppm): 2.32 (s, 3H), 2.55 (s, 3H), 3.31-3.33 (d, 3H), 7.22 (s, 1H), 7.36-7.41 (m, 3H), 7.63-7.68 (m, 3H & 1H D$_2$O exchangeable), 7.9-7.94 (m, 1H), 14.69 (s, 1H, D$_2$O exchangeable); IR (KBr) cm$^{-1}$: 3433, 3375, 1651 and 1555; MS m/z: 433.0 (M$^+$+1). |
| 53 | 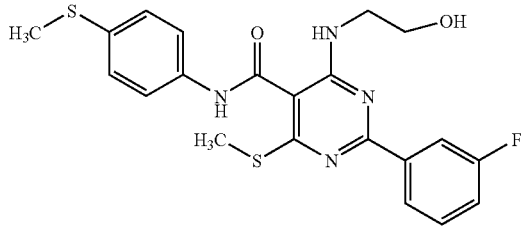<br>m.p.: 160–165° C. | Purity (HPLC): 98.1%; $^1$H-NMR (DMSO-d$_6$) δ (ppm): 2.46 (s, 3H), 2.59 (s, 3H), 3.58 (s, 4H), 4.78 (s, 1H, D$_2$O exchangeable), 7.12 (s, 1H, D$_2$O exchangeable), 7.27-7.29 (d, 2H), 7.38-7.38 (d, 1H), 7.57-7.58 (d, 1H), 7.65-7.67 (d, 2H), 8.08-8.1 (d, 1H), 8.24-8.26 (d, 1H), 10.52 (s, 1H, D$_2$O exchangeable); IR (KBr) cm$^{-1}$: 3393, 3284, 1625 and 1530;MS m/z: 445.0 (M$^+$+1). |
| 54 | 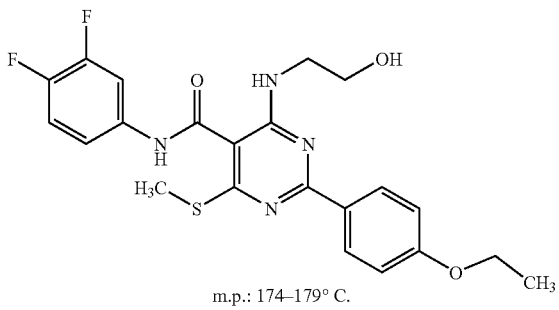<br>m.p.: 174–179° C. | Purity (HPLC): 95.1%; $^1$H-NMR (CDCl$_3$) δ (ppm): 1.43-1.47 (t, 3H), 2.75 (s, 3H), 3.53-3.55 (m, 1H), 3.79-3.82 (m, 2H), 3.87-3.9 (m, 2H), 4.1-4.13 (q, 2H), 6.95-6.97 (d, 2H), 7.14-7.18 (d, 2H), 7.69-7.72 (m, 1H), 8.35-8.37 (m, 3H, 1H is D$_2$O exchangeable), 8.46 (s, 1H, D$_2$O exchangeable); IR (KBr) cm$^{-1}$: 3387, 3385, 2923, 1651, 1606 and 1584;MS m/z: 461.1 (M$^+$+1). |
| 55 | 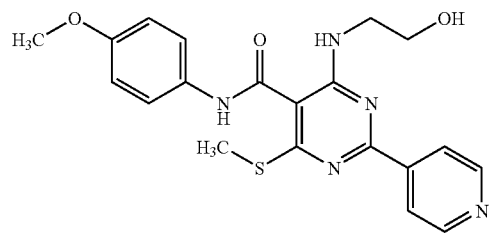<br>m.p.: 242–245° C. | Purity (HPLC): 98.7%; $^1$H-NMR (DMSO-d$_6$) δ (ppm): 2.60 (s, 3H), 3.58 (s, 4H), 3.74 (s, 3H), 4.79 (s, 1H, D$_2$O exchangeable), 6.92-6.94 (d, 2H), 7.15 (s, 1H, D$_2$O exchangeable), 7.61-7.63 (d, 2H), 8.25-8.26 (d, 2H), 8.75-8.76 (d, 2H), 10.41 (s, 1H, D$_2$O exchangeable); IR (KBr) cm$^{-1}$: 3397, 3350, 2935, 1665 and 1512; MS m/z: 412.1 (M$^+$+1). |

-continued

| Exp. | Structure | Analytical data |
|---|---|---|
| 56 | 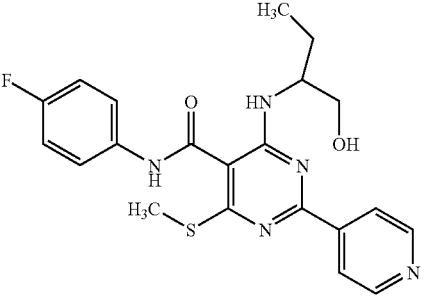<br>m.p.: 250–253° C. | Purity (HPLC): 97.9%; $^1$H-NMR (DMSO-d$_6$) δ (ppm): 0.71-0.75 (t, 3H), 2.01-2.04 (m, 1H), 1.98-1.99 (m, 1H), 2.33 (s, 3H), 3.57-3.58 (m, 1H), 4.0-4.03 (m, 1H), 4.1 (s, 1H), 5.11-5.14 (t, 1H, D$_2$O exchangeable), 7.17-7.21 (t, 2H), 7.66-7.72 (m, 4H), 8.81-8.82 (d, 2H), 11.50 (s, 1H, D$_2$O exchangeable); IR (KBr) cm$^{-1}$: 3451, 2930, 1668 and 1526;MS m/z: 429.1 (M$^+$+1). |
| 57 | 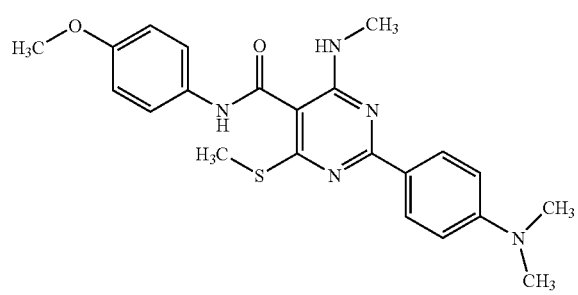 | Purity (HPLC): 96.0%; $^1$H-NMR (DMSO-d$_6$) δ (ppm): 2.56 (s, 3H), 2.94-2.95 (d, 3H), 3.0 (s, 6H), 3.73 (s, 3H), 6.77-6.79 (d, 2H), 6.85-6.86 (d, 1H, D$_2$O exchangeable), 6.9 (s, 2H), 7.6-7.62 (d, 2H), 8.24-8.26 (d, 2H), 10.24 (s, 1H, D$_2$O exchangeable); MS m/z: 424.1 (M$^+$+1). |
| 58 | 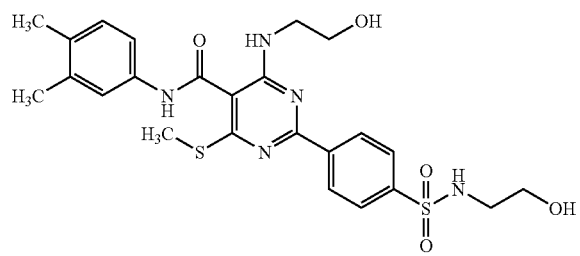 | Purity (HPLC): 90.5%; $^1$H-NMR (DMSO-d$_6$) δ (ppm): 2.31 (s, 3H), 2.84 (s, 3H), 3.37 (s, 3H) 3.56-3.59 (m, 8H), 4.71-4.78 (d, 2H, D$_2$O exchangeable), 7.11 (s, 1H, D$_2$O exchangeable), 7.52 (s, 3H), 7.68 (s, 2H & 1H is D$_2$O exchangeable), 8.12 (s, 1H), 8.4 (s, 2H), 10.63 (s, 1H, D$_2$O exchangeable); IR (KBr) cm$^{-1}$: 3399, 2929, 1654 and 1586; MS m/z:532.1 (M$^+$+1). |

EXAMPLE 59

To the clear solution of N-(4-Methoxyphenyl)-4-(methylamino)-6-(methylthio)-2-pyridin-3-ylpyrimidine-5-carboxamide (2.5 g, 6.55 mmol, prepared according to the procedure described in example 5) in acetone (250 ml) was added orthophosphoric acid (1.6 g, 16.38 mmol) in one portion under stirring. The stirring was continued until the solid separates out. The resultant solid was filtered and washed slowly and dropwise with acetone (5 ml). The solid obtained was dried under vacuum to yield the desired salt 3.78 g, yield 97.8%, assay of base 68.3% by HPLC and phosphate content 30.09% by assay, m.p.: 222-225° C. $^1$H-NMR (DMSO-d$_6$) δ (ppm): 2.59 (s, 3H), 2.96-2.98 (d, 3H), 3.74 (s, 3H), 6.91-6.94 (m, 2H), 7.12-7.14 (m, 1H, D$_2$O exchangeable), 7.54-7.57 (m, 1H), 7.61-7.63 (m, 2H), 8.67-8.71 (m, 2H), 9.53 (s, 1H), 10.39 (s, 1H, D$_2$O exchangeable). IR (KBr) cm$^{-1}$: 3788.5, 3388, 1722, 1686, 1657, 1615, 1580 and 1548. MS m/z: 382.1 (M$^+$+1).

General Procedure for Making Salts:

To the suspension/solution of N,2-Diaryl-4-(methylamino)-6-(methylthio)-pyrimidine-5-carboxamide (prepared according to the procedure described in the above examples) in a suitable solvents like ethanol, isopropanol, dichloromethane, ethylacetate, hexane, THF, acetone, ether, acetonitrile, dioxane or the combination/mixture of solvents mentioned in 1:1 to 1:10 ratio was added 3 to 10 molar quantities of acid which includes aqueous hydrochloric acid or dry hydrogen chloride gas, orthophosphoric acid, nitric acid, sulphuric acid, succinic acid, oxalic acid, citric acid, salicylic acid, methane sulfonic acid, p-toluene sulfonic acid, benzoic acid etc of inorganic/organic origin under stirring at an ambient temperature to reflux temperature. Subsequently a solid separated out or was precipitated out by adding a suitable solvent, it was filtered or the solvent was removed under vacuum. This resulted in the target salts as mono or di or tri salts in a pure form. The salts thus formed were characterized by using analytical techniques and estimations.

The Following Salts are Prepared by the General Procedure Given Above.

| 60 | 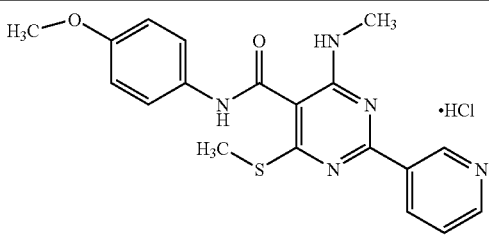 m.p.: 240–244° C. | Assay of base (HPLC): 88.8%; $^1$H-NMR (DMSO-$d_6$) δ (ppm): 2.61 (s, 3H), 2.98-2.99 (d, 3H), 3.74 (s, 3H), 6.92-6.94 (m, 2H), 7.24-7.25 (m, 1H, D$_2$O exchangeable), 7.61-7.64 (m, 2H), 7.88-7.91 (m, 1H), 8.88-8.89 (m, 1H), 9.04-9.06 (m, 1H), 9.59 (s, 1H), 10.43 (s, 1H, D$_2$O exchangeable); IR (KBr) cm$^{-1}$: 3401, 3265, 2100, 1980, 1641, 1613, 1579 and 1512; MS m/z: 382.1 (M$^+$+1). |
| --- | --- | --- |
| 61 | 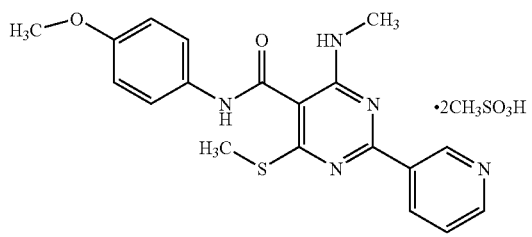 m.p.: 219–223° C. | Assay of base (HPLC): 69.9%; $^1$H-NMR (DMSO-$d_6$) δ (ppm): 2.34 (s, 3H), 2.62 (s, 3H), 2.98-2.99 (d, 3H), 3.74 (s, 3H), 6.92-6.94 (m, 2H), 7.29-7.3 (m, 1H, D$_2$O exchangeable), 7.61-7.63 (m, 2H), 8.0-8.04 (m, 1H), 8.95-8.96 (m, 1H), 9.17-9.19 (m, 1H), 9.63 (s, 1H), 10.45 (s, 1H, D$_2$O exchangeable); IR (KBr) cm$^{-1}$: 3415, 3232, 3014, 1651, 1608, 1579, 1535, 1424, 1324 and 1301; MS m/z:382.1 (M$^+$+1). |
| 62 | 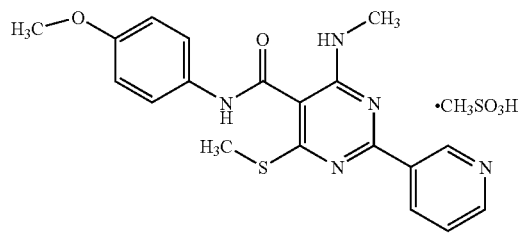 m.p.: 201–203° C. | Assay of base (HPLC): 76.7%; $^1$H-NMR (DMSO-$d_6$) δ (ppm): 2.34 (s, 3H), 2.61 (s, 3H), 2.98-2.99 (d, 3H), 3.74 (s, 3H), 6.92-6.94 (m, 2H), 7.28-7.29 (m, 1H, D$_2$O exchangeable), 7.61-7.63 (m, 2H), 7.99-8.0 (m, 1H), 8.94-8.95 (m, 1H), 9.17-9.19 (m, 1H), 9.62 (s, 1H), 10.44 (s, 1H, D$_2$O exchangeable); IR (KBr) cm$^{-1}$: 3415, 3261, 2139, 1651, 1608, 1579 and 1535; MS m/z: 382.1 (M$^+$+1). |
| 63 | 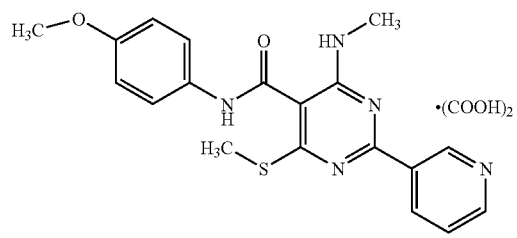 m.p.: 210–214° C. | Assay of base (HPLC): 78.8%; $^1$H-NMR (DMSO-$d_6$) δ (ppm): 2.59 (s, 3H), 2.97-2.98 (d, 3H), 3.74 (s, 3H), 6.92-6.94 (m, 2H), 7.14-7.15 (m, 1H, D$_2$O exchangeable), 7.52-7.58 (m, 1H), 7.62-7.64 (m, 1H), 8.68-8.7 (m, 1H), 9.54 (s, 1H), 10.4 (s, 1H, D$_2$O exchangeable), 14.1 (s, 1H, D$_2$O exchangeable); IR (KBr) cm$^{-1}$: 3396, 3107, 1734, 1634, 1576, 1529 and 1513; MS m/z: 382.1 (M$^+$+1). |
| 64 | 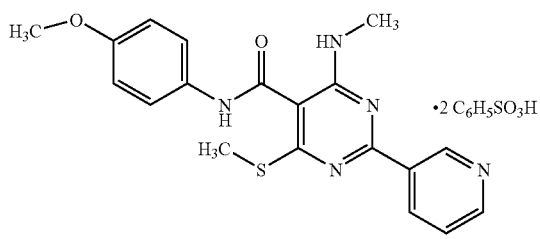 m.p.: 182–185° C. | Assay of base (HPLC): 53.6%; $^1$H-NMR (DMSO-$d_6$) δ (ppm): 2.61 (s, 3H), 2.97-2.98 (d, 3H), 3.74 (s, 3H), 6.92-6.94 (m, 2H), 7.3-7.34 (m, 6H, 1H is D$_2$O exchangeable), 7.58-7.63 (m, 5H), 7.98-8.0 (m, 1H), 8.93-9.1 (m, 1H), 9.61(s, 1H), 10.43 (s, 1H, D$_2$O exchangeable), 14.1 (s, 1H, D$_2$O exchangeable); IR (KBr) cm$^{-1}$: 3421, 3246, 2118, 1672, 1608, 1551, 1509 and 1445; MS m/z: 381.9 (M$^+$+1). |

Described below are the examples of pharmacological assays used for finding out the efficacy of the compounds of the present invention wherein their protocols and results are provided.

In Vitro Evaluation of Cyclooxygenase-2 (COX-2) Inhibition Activity

The compounds of this invention exhibited in vitro inhibition of COX-2. The COX-2 inhibition activities of the compounds illustrated in the examples were determined by the following method.

Human Whole Blood Assay

Human whole blood provides a protein and cell rich milieu appropriate for the study of biochemical efficacy of anti-inflammatory compounds such as selective COX-2 inhibitors. Studies have shown that normal human blood does not contain COX-2 enzyme. This is correlating with the observation that COX-2 inhibitors have no effect on prostaglandin $E_2$ ($PGE_2$) production in normal blood. These inhibitors were active only after incubation of human blood with lipopolysaccharide (LPS), which induces COX-2 production in the blood.

Fresh blood was collected in tubes containing sodium heparin by vein puncture from healthy male volunteers. The subjects should have no apparent inflammatory conditions and should have not taken NSAIDs for at least 7 days prior to blood was pre-incubated with aspirin in vitro (12 µg/ml, at time zero) to inactive COX-1 for 6 hours. Then test compounds (at various concentrations) or vehicle were added to blood. After that blood was stimulated with LPS B: 4 (10 µg/ml) and incubated for another 18 hours at 37° C. water bath. After which the blood was centrifuged, plasma was separated and stored at −80° C. (J. Pharmacol. Exp. Ther, 271, 1705, 1994; Proc. Natl. Acad. Sci. USA., 96, 7563, 1999). The plasma was assayed for PGE2 using Cayman ELISA kit as per the procedure outlined by the manufacturer (Cayman Chemicals, Ann Arbor, USA). Representative results of COX-2 inhibition are shown in the Table I.

TABLE I

| Example No. | Conc. (µM) | COX-2 Inhibition (%) |
| --- | --- | --- |
| 5 | 0.25 | 36.75 |
| 9 | 10 | 29.19 |
| 10 | 10 | 24.2 |
| 12 | 0.25 | 24.92 |
| 13 | 0.25 | 24.5 |

COX-1 and COX-2 Enzyme Based Assay

COX-2 enzyme based assays were carried out to check the inhibitory potential of test compounds on the production of prostaglandin by purified recombinant COX-1/COX-2 enzyme (Proc. Nat. Acad. Sci. USA, 88, 2692-2696, 1991; Clin. Immunoassay 15, 116-120, 1992) In this assay, the potential of the test compound to inhibit the production of prostaglandin either by COX-1 or COX-2 from arachidonic acid (substrate) was measured. This was an enzyme based in-vitro assay to evaluate selective COX inhibition with good reproducibility.

Arachidonic acid was converted to PGH2 (Intermediate product) by COX1/COX-2 in presence or absence of the test compound. The reaction was carried out at 37° C. and after 2 minutes it was stopped by adding 1M HCl. Intermediate products PGH2 was converted to a stable Prostanoid product PGF2α by $SnCl_2$ reduction. The amount of PGF2α produced in the reaction was inversely proportional to the COX inhibitory potential of the test compound. The prostanoid product was quantified via enzyme immunoassay (EIA) using a broadly specific antibody that binds to all the major forms of Prostaglandin, using Cayman ELISA kit as per the procedure outlined by the manufacturer Cayman Chemicals, Ann Arbor, USA). Representative results of inhibition are shown in the Table II.

TABLE II

| Example No. | Conc. (µM) | COX-1 Inhibition (%) | COX-2 Inhibition (%) |
| --- | --- | --- | --- |
| 6 | 10 | 28.76 | 19.3 |
| 14 | 10 | Not Active | 11.38 |
| 28 | 10 | 25.5 | 23.16 |
| 35 | 10 | 15.22 | 26.84 |
| 37 | 10 | 6.58 | 17.07 |

In Vitro Measurement of Tumor Necrosis Factor Alpha (TNF-α)

This assay determines the effect of test compounds on the production of TNF-α in human Peripheral Blood Mononuclear Cells (PBMC). Compounds were tested for their ability to inhibit the activity of TNF-α in human PBMC. PBMC were isolated from blood (from healthy volunteers) using BD Vacutainer CPT™ (Cell preparation tube, BD Bio Science) and suspended in RPMI medium (Physiol. Res. 52; 593-598, 2003). The test compounds were pre-incubated with PBMC (0.5 million/incubation well) for 15 minutes at 37° C. and then stimulated with Lipopolysaccharide (*Escherichia coli*: B4; 1 µg/ml) for 18 hours at 37° C. in 5% $CO_2$. The levels of TNF-α in the cell culture medium were estimated using enzyme linked Immunosorbent assay performed in a 96 well format as per the procedure of the manufacturer (R&D Systems, Inc. 614 McKinley Place Nebr., Minneapolis, Minn. 55413, USA). Representative results of TNF-α inhibition are shown in Table III.

TABLE III

| Example No. | TNF-α Inhibition (%) | $IC_{50}$ (µM) |
| --- | --- | --- |
| 6 | 30.31 at 0.1 µM | 0.86 |
| 7 | 30.38 at 0.1 µM | — |
| 8 | 27.76 at 0.1 µM | — |
| 14 | 36.82 at 1 µM | — |
| 16 | 53.08 at 10 µM | — |
| 17 | 30.06 at 0.1 µM | — |
| 28 | 45.13 at 1 µM | 0.9 |
| 35 | 52.71 at 1 µM | 1.8 |
| 37 | 42.67 at 1 µM | 1.5 |

In vitro Measurement of Interleukin-6 (IL-6) & Interleukin-1β (IL1β)

This assay determines the effect of test compounds on the production of IL-6 and IL1β in human PBMC (Physiol. Res. 52: 593-598, 2003). Compounds were tested for their ability to inhibit the activity of IL-6 and IL1β in human PBMC. PBMC were isolated from blood using BD Vacutainer CPT™ Cell preparation tube (BD Bio Science) and suspended in RPMI medium. The test compounds were preincubated with PBMC (0.5 million/incubation well) for 15 minutes at 37° C. and then stimulated with Lipopolysaccharide (*Escherichia coli*: B4; 1 µg/ml) for 18 hours at 37° C. in 5% $CO_2$. The levels of IL-6 and IL1β in cell culture medium were estimated using enzyme linked Immunosorbent assay performed in a 96 well format as per the procedure of the manufacturer (R&D Systems, Inc. 614 McKinley Place Nebr., Minneapolis, Minn. 55413, USA). Representative results of IL-6 and IL-1β inhibition are shown in Table IV.

TABLE IV

| Example No. | Conc. (μM) | IL-6 Inhibition (%) | IL-1β Inhibition (%) |
|---|---|---|---|
| 5 | 0.1 | 14.93 | Not active |
| 7 | 10 | 53.81 | Not active |
| 13 | 0.1 | 21.46 | Not active |
| 14 | 0.1 | 28.18 | Not active |
| 36 | 0.1 | 26.56 | Not active |
| 40 | 10 | 61.54 | Not active |
| 42 | 10 | 92.21 | Not active |

Carrageenan Induced Paw Edema Test in Rat

The carrageenan paw edema test was performed as described by Winter et al (Proc. Soc. Exp. Biol. Med, 111, 544, 1962). Male wistar rats were selected with body weights equivalent within each group. The rats were fasted for eighteen hours with free access to water. The rats were dosed orally with the test compound suspended in vehicle containing 0.25% carboxymethylcellulose and 0.5% Tween 80. The control rats were administered with vehicle alone. After an hour, the rats were injected with 0.1 ml of 1% Carrageenan solution in 0.9% saline into the sub-plantar surface of the right hind paw. Paw volume was measured using digital plethysmograph before and after 3 hours of carrageenan injection. The average of foot swelling in drug treated animals was compared with that of control animals. Anti-inflammatory activity was expressed as the percentage inhibition of edema compared with control group [Arzneim-Forsch/Drug Res., 43 (I), 1,44-50,1993; Otterness and Bliven, Laboratory Models for Testing NSAIDs, In Non-Steroidal Anti-Inflammatory Drugs, (J. Lombardino, ed. 1985)]. Representative results of edema inhibition are shown in Table V.

TABLE V

| Example No. | Inhibition of edema (%) at 5 mg/kg |
|---|---|
| 5 | 53.07 |
| 14 | 31.02 |

Ulcerogenic Potential

In order to evaluate compound's role on the ulcer formation, the animals were sacrificed and the stomach was taken out and flushed with 1% formalin. Animals (male wistar 200 gm) were fasted for 18 hours free access to water and the test compounds were suspended in 0.5% Tween 80 and 0.25% CMC (carboxymethylcellulose) solution to make a uniform suspension. After 4 hours of oral administration of test compounds, all the animals were sacrificed by cervical dislocation. Dissect the stomach carefully and filled up with a sterile saline solution and embedded in 6% formalin solution. Finally cut the stomach longnitudinaly and ulcer lesions were observed with computerized stereomicroscope. Compare the test compound treated groups with the vehicle treated groups. Dose selected: 50, 100, 200 mg/kg (Marco Romano et al, Journal of clinical Investigation, 1992; 2409-2421)

Inhibitory Action on Adjuvant Arthritis in Rats

Compounds were assayed for their activity on rat adjuvant induced arthritis model according to Theisen-Popp et al., (Agents Actions, 42, 50-55, 1994). Six to seven weeks old, wistar rats were weighed, marked and assigned to groups [a negative control group in which arthritis was not induced (non-adjuvant control), a vehicle-treated arthritis control group, test substance treated arthritis group]. Adjuvant induced arthritis was induced by an injection of 0.1 ml of Mycobacterium butyricum (Difco) suspended in mineral oil (5 mg/ml) into the sub-plantar region of the right hind paw (J. Pharmacol. Exp. Ther., 284, 714, 1998). Body weight, paw volumes were measured at various days (0, 4, 14, 21) for all the groups. The test compound or vehicle was administered orally beginning post injection of adjuvant ('0'day) and continued for 21 days (pretreatment group). In post treatment group, the test compound or vehicle was administered starting from day $14^{th}$ to $21^{st}$ day. On day 21, body weight and paw volume of both right and left hind paw were taken. Spleen, and thymus weights were determined. In addition, the radiographs of both hind paws were taken to assess the tibio-tarsal joint integrity. Hind limb below the stifle joint was removed and fixed in 1% formalin saline for the histopathological assessment. At the end of the experiment, serum samples were analysed for inflammatory mediators. The presence or absence of lesions in the stomach was also observed. Two-factor ('treatment' and 'time') analysis of variance with repeated measures on 'time' was applied to the percentage (%) changes for body weight and foot volumes. A post hoc Dunnett's test was conducted to compare the effect of treatments to vehicle control. A one-way analysis of variance was applied to the thymus and spleen weights followed by the Dunnett's test to compare the effect of treatments to vehicle. Dose-response curves for percentage inhibition in foot volumes on days 4, 14 and 21 were fitted by a 4-parameter logistic function using a nonlinear least Squares' regression. $IC_{50}$ was defined as the dose corresponding to a 50% reduction compared to vehicle control and was derived by interpolation from the fitted 4-parameter equation.

LPS Induced Sepsis for Measurement of TNF-α Inhibition in Mice

The LPS induced sepsis model in mice was performed as described by Les sekut et al (J Lab Clin Med 1994; 124:813-20). Female Swiss albino mice were selected with their body weights being equivalent within each group. The mice were fasted for 20 hours with free access to water. The mice were dosed orally with the test compound suspended in vehicle containing 0.5% Tween 80 in 0.25% Carboxy-methylcellulose sodium salt. The control mice were administered the vehicle alone. After 30 minutes of oral dosing, the mice were injected with 500 μg of Lipopolysaccharide (Escherichia coli, LPS: B4 from Sigma) in phosphate buffer saline solution into the intraperitoneal cavity of the mice. After 90 minutes of LPS administration, the mice were bled via retro-orbital sinus puncture. Blood samples were stored overnight at 4° C. Serum samples were collected by centrifuging the samples at 4000 rpm for 15 minutes at 4° C. Immediately the serum samples were analysed for TNF-α levels, using commercially available mouse TNF-α ELISA kit (Amersham Biosciences) and assay was performed by the manufacturer instruction. Representative results of TNF-α inhibition are shown in Table VI.

TABLE VI

| Example No. | TNF-α Inhibition (%) at 50 mg/kg bw |
|---|---|
| 6 | 77.0 |
| 14 | 18.74 |
| 28 | 81.5 |

TABLE VI-continued

| Example No. | TNF-α Inhibition (%) at 50 mg/kg bw |
|---|---|
| 35 | 59.94 |
| 37 | 66.65 |

Anti-Cancer Screen:

Experimental drugs are screened for anti-cancer activity in three cell lines for their $GI_{50}$, TGI and $LC_{50}$ values (using five concentrations for each compound). The cell lines are maintained in DMEM containing 10% fetal bovine serum. 96 well microtiter plates are inoculated with cells in 100 μL for 24 h at 37° C., 5% CO2, 95% air and 100% relative humidity. 5000 HCT116 cells/well, 5000 NCIH460 cells/well, 10000 U251 cells/well and 5000 MDAMB231 cells/well are plated. A separate plate with these cell lines is also inoculated to determine cell viability before the addition of the compounds ($T_0$).

Addition of Experimental Drugs

Following 24 hours incubation, experimental drugs are added to the 96 well plates. Each plate contains one of the above cell lines and the following in triplicate: five different concentrations (0.01, 0.1, 1, 10 and 100 μM) of four different compounds, appropriate dilutions of a cytotoxic standard and control (untreated) wells. Compounds are dissolved in dimethylsulfoxide (DMSO) to make 20 mM stock solutions on the day of drug addition and frozen at −20° C. Serial dilutions of these 20 mM stock solutions are made in complete growth medium such that 100 μL of these drug solutions in medium, of final concentrations equaling 0.01, 0.1, 1, 10 and 100 μM can be added to the cells in triplicate. Standard drugs whose anti-cancer activity has been well documented and which are regularly used are doxorubicin and SAHA.

End-Point Measurement

Cells are incubated with compounds for 48 hours followed by the addition of 10 μL 3-(4,5-Dimethyl-2-thiazolyl)-2,5-diphenyl-2H-tetrazolium (MTT) solution per well and a subsequent incubation at 37° C., 5% $CO_2$, 95% air and 100% relative humidity, protected from light. After 4 hours, well contents are aspirated carefully followed by addition of 150 μL DMSO per well. Plates are agitated to ensure solution of the formazan crystals in dimethylsulphoxide and absorbance read at 570 nm.

Calculation of $GI_{50}$, TGI and $LC_{50}$

Percent growth is calculated for each compound's concentration relative to the control and zero measurement wells (To; viability right before compound addition). If a test well's O.D. value is greater than the To measurement for that cell line % Growth=(test−zero)/(control−zero)×100

If a test well's O.D. value is lower than the $T_0$ measurement for that cell line, then % Growth=(test−zero)/zero×100

Plotting % growth versus experimental drug concentration, $GI_{50}$ is the concentration required to decrease % growth by 50%; TGI is the concentration required to decrease % growth by 100% and $LC_{50}$ is the concentration required to decrease % growth by 150%. Representative results of growth are shown in Table VII and VIII.

TABLE VII

| | | Percentage growth | | |
|---|---|---|---|---|
| Example No. | Conc. (μM) | Lung NCI-H460 | Breast MCF-7 | CNS SF-268 |
| 5 | 50 | 48 | 160 | 106 |
| 8 | 100 | 0 | 4 | 1 |
| 9 | 100 | 0 | 6 | 5 |

TABLE VIII

| | $GI_{50}$ | | | | |
|---|---|---|---|---|---|
| Example No. | NCI-H460 | HCT116 | DU145 | U251 | MDAMB-231 |
| 14 | 5.15 | — | 2.75 | — | — |
| 18 | 2 | 1.2 | — | — | — |
| 20 | 3.2 | — | — | — | — |
| 21 | 0.4 | 9.5 | — | — | — |
| 24 | 4 | 9.9 | — | — | — |
| 25 | 5.5 | — | — | — | 0.1 |
| 32 | — | 4 | — | 3 | — |
| 34 | 0.9 | 9 | — | — | — |
| 35 | 9 | — | — | — | — |
| 24 | 4 | 9.9 | — | — | — |
| 25 | 5.5 | — | — | — | 0.1 |
| 32 | — | 4 | — | 3 | — |
| 34 | 0.9 | 9 | — | — | — |
| 35 | 9 | — | — | — | — |
| 36 | 3 | — | — | 1.8 | — |
| 39 | 2 | — | — | 0.09 | — |
| 40 | 0.5 | 2 | — | 0.1 | — |
| 42 | 3 | 4 | — | 5 | — |
| 45 | 0.4 | — | — | 0.7 | — |
| 46 | 0.2 | — | — | 0.2 | — |
| 47 | 0.1 | — | — | 0.3 | — |
| 48 | 5 | 2.5 | — | 3 | — |
| 57 | 7 | — | — | 4 | — |

We claim:

1. A compound of formula (I),

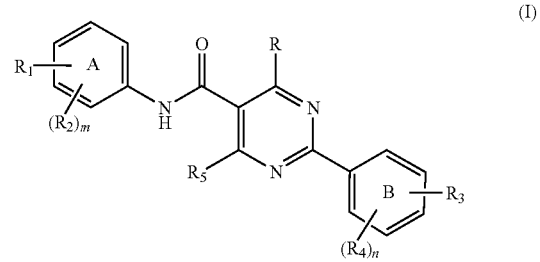

and pharmaceutically acceptable salts thereof;

wherein a ring system represented by A is selected from phenyl, naphthyl, pyridyl, thienyl, and pyrimidinyl, which may be substituted;

wherein a ring system represented by B is selected from phenyl, naphthyl, pyridyl, thienyl, pyrimidinyl, which may be substituted;

wherein R independently represents halogen, hydroxyl, azido, amino, linear or branched ($C_1$-$C_4$) alkyl group; haloalkyl group; $SR_6$, $S(O)_qR_7$; aminocycloalkyl group; monoalkylamino group which may be substituted; dialkylamino group; —NH($C_1$-$C_5$)$_n$—X, wherein ($C_1$-$C_5$) alkyl group is linear or branched and, X is aryl or heteroaryl, aryl group and heteroaryl group; heterocyclyl group; aminoheterocyclyl group; aminoalkanols; hydrazine; or alkylhydrazines;

wherein $R_1$ is selected from hydrogen, $SR_6$ and $S(O)_pR_7$;

wherein $R_2$ is selected from hydrogen or a halogen atom; hydroxyl, nitro, cyano, azido, amino, linear or branched $(C_1-C_4)$ alkyl group; haloalkyl group; linear or branched $(C_1-C_6)$ alkoxy group; aminoalkyl group; aminodialkyl group; acyl group; aminoacyl group; alkoxycarbonyl group; alkoxyalkyl group; $COR_8$; carboxylic acid; and carboxylic acid derivatives selected from the group consisting of esters, amides and acid halides of carboxylic acids;

wherein $R_3$ is selected from hydrogen, $SR_6$ and $S(O)_pR_7$;

wherein $R_4$ is selected from hydrogen or a halogen atom; hydroxyl, nitro, cyano, azido, amino, linear or branched $(C_1-C_4)$ alkyl group; haloalkyl group; linear or branched $(C_1-C_6)$ alkoxy group; aminoalkyl group; aminodialkyl group; acyl group; aminoacyl group; alkoxycarbonyl group; alkoxyalkyl group; $COR_8$; carboxylic acid; and carboxylic acid derivatives selected from the group consisting of esters, amides and acid halides of carboxylic acids;

wherein $R_5$ independently represents hydrogen, hydroxyl, azido, amino, linear or branched $(C_1-C_4)$ alkyl group; haloalkyl group; $SR_6$, $S(O)_qR_7$; aminocycloalkyl group; monoalkylamino group which may be substituted; dialkylamino group; $-NH(C_1-C_5)_n-X$, wherein $(C_1-C_5)$ alkyl group is linear or branched and X is aryl or heteroaryl, aryl group; heteroaryl group; heterocyclyl group; aminoheterocyclyl group; aminoalkanol; hydrazine; or alkylhydrazine;

wherein $R_6$ is selected from hydrogen, linear or branched $(C_1-C_6)$ alkyl group; aryl group and alkylester;

wherein $R_7$ is selected from amino, hydroxyl, hydrazine, halogen atom; linear or branched $(C_1-C_6)$ alkyl group; alkylhydrazine group; acylhydrazide group; aminoacyl group; aminoalkanol; aryl group; aminoaryl group; aminoheteroaryl group; and aminoheterocyclyl group;

wherein $R_8$ is selected from hydrogen, hydroxyl, amino, halogen atom; linear or branched $(C_1-C_4)$ alkyl group; haloalkyl group; linear or branched $(C_1-C_4)$ alkoxy group; aryloxy group; aminoalkyl group which may be substituted; dialkylamino group; arylamino group; heteroarylamino group and acylamino group;

wherein m and n are integers ranging from 0 to 4; p is an integer of 1 or 2; q is an integer in the range of 1 to 10; and wherein if B is phenyl, one or more of R, $R_1$, $R_3$ and $R_5$ is $SR_6$, $S(O)_pR_7$ or $S(O)_qR_7$.

2. The compound of claim 1 selected from a group consisting of:

4-Hydroxy-N-(4-methylphenyl)-6-(methylthio)-2-[4-(methylthio)phenyl]pyrimidine-5 -carboxamide;

4-Hydroxy-N-(3,4-dimethylphenyl)-6-(methylthio)-2-[4-methylthio)phenyl]pyrimidine-5-carboxamide;

2-(4-Fluorophenyl)-4-hydroxy-6-(methylthio)-N-[4-(methylthio)phenyl]pyrimidine-5-carboxamide;

4-Chloro-N-(4-methylphenyl)-6-(methylthio)-2-[4-(methylthio)phenyl]pyrimidine-5-carboxamide;

4-(Methylamino)-N-(4-methylphenyl)-6-(methylthio)-2-[4-(methylthio)phenyl]pyrimidine-5-carboxamide;

N-(4-Methoxyphenyl)-4-(methylamino)-6-(methylthio)-2-pyridin-3-ylpyrimidine-5-carboxamide;

N-(3,4-Dimethylphenyl)-4,6-bis(methylamino)-2-pyridin-3-ylpyrimidine-5-carboxamide;

N-(4-Ethylphenyl)-4-(methylamino)-6-(methylthio)-2-[4-(methylthio)phenyl]pyrimidine-5-carboxamide;

N-(3,4-Dimethylphenyl)-4-(methylamino)-6-(methylthio)-2-[4-(methylthio)phenyl]pyrimidine-5-carboxamide;

2-[4-(Aminosulfonyl)phenyl]-4,6-bis(methylamino)-N-(3,4-dimethylphenyl)pyrimidine-5-carboxamide;

2-[4-(Aminosulfonyl)phenyl]-N-(3,4-dimethylphenyl)-4-(methylamino)-6-(methylthio)pyrimidine-5-carboxamide;

2-[4-(Amninosulfonyl)phenyl]-4-(methylamino)-N-(4-methylphenyl)-6-(methylthio)pyrimidine-5-carboxamide;

2-[4-(Aminosulfonyl)phenyl]-4,6-bis(methylamino)-N-(4-methylphenyl)pyrimidine-5-carboxamide;

N-(4-Methoxyphenyl)-4-(methylamino)-6-(methylthio)-2-pyridin-4-ylpyrimidine -5-carboxamide;

N-(4-Ethoxyphenyl)-4,6-bis(methylamino)-2-pyridin-4-ylpyrimidine-5-carboxamide;

2-[4-(Aminosulfonyl)phenyl]-4,6-bis(methylamino)-N-(4-ethylphenyl) pyrimidine-5-carboxamide;

2-[4-(Aminosulfonyl)phenyl]-N-(4-ethylphenyl)-4-(methylamino)-6-(methylthio)pyrimidine-5-carboxamide;

N-(4-Fluorophenyl)-4-(methylamino)-6-(methylthio)-2-pyridin-4-ylpyrimidine-5-carboxamide;

4-(Methylamino)-2-[4-(methylsulfinyl)phenyl]-N-(4-methoxyphenyl)-6-(methylthio)pyrimidine-5-carboxamide;

4-(Methylamino)-N-(4-methoxyphenyl)-6-(methylthio)-2-[4-(methylthio)phenyl]pyrimidine-5-carboxamide;

N-(4-Ethylphenyl)-4-(methylamino)-6-(methylthio)-2-pyridin-4-ylpyrimidine-5-carboxamide;

N-(4-Ethylphenyl)-4-(methylamino)-6-(methylthio)-2-pyridin-3-ylpyrimidine-5-carboxamide;

4-[(2-Hydroxyethyl)amino]-N-(4-methoxyphenyl)-6-(methylthio)-2-pyridin-3-ylpyrimidine-5-carboxamide;

4-(Methylamino)-N-(4-methylphenyl)-6-(methylthio)-2-pyridin-4-ylpyrimidine-5-carboxamide;

N-(3,4-Dimethylphenyl)-4-(methylamino)-6-(methylthio)-2-pyridin-4-ylpyrimidine-5-carboxamide;

N-(3,4-Dimethylphenyl)-4,6-bis(methylamino)-2-pyridin-4-ylpyrimidine -5-carboxamide;

4,6-Bis(methylamino)-N-(4-methylphenyl)-2-pyridin-4-ylpyrimidine-5-carboxamide;

N-(4-Methoxyphenyl)-4,6-bis(methylamino)-2-pyridin-3-ylpyrimidine-5-carboxamide;

N-(4-Fluorophenyl)-4-[(2-hydroxyethyl)amino]-6-(methylthio)-2-pyridin-4-ylpyrimidine-5-carboxamide;

4-[(2-Hydroxyethyl)amino]-N-(4-methoxyphenyl)-6-(methylthio)-2-[4-(methylthio)phenyl]pyrimidine-5-carboxamide;

N-(4-Ethylphenyl)-4-[(2-hydroxyethyl)amino]-6-(methylthio)-2-pyridin-4-ylpyrimidine-5 -carboxamide;

N-(3,4-Dimethylphenyl)-4-[(2-hydroxyethyl)amino]-6-(methylthio) -2-[4-(methylthio)phenyl]pyrimidine-5 -carboxamide;

N-(4-Isoproylphenyl)-4-(methylamino)-6-(methylthio)-2-pyridin-3 -ylpyrimidine-5-carboxamide;

N-(4-Isoproylphenyl)-4-(methylamino)-6-(methylthio)-2-pyridin-4-ylpyrimidine-5-carboxamide;

4-[(2-Hydroxyethyl)amino]-N-(4-methylphenyl)-6-(methylthio)-2-pyridin-4-ylpyrimidine-5-carboxamide;

N-(4-Butylphenyl)-4-[(2-hydroxyethyl)amino]-6-(methylthio)-2-[4-(methylthio)phenyl]pyrimidine-5-carboxamide;

N-(3,4-Dimethypheny1)-4-[(2-hydroxyethyl)amino]-6-(methylthio)-2-pyridin-4-ylpyrimidine-5-carboxamide;

4-(Methylamino)-6-(methylthio)-N,2-bis[4-(methylthio)phenyl]pyrimidine-5-carboxamide;

N-(2,4-Dimethylphenyl)-4-(methylamino)-6-(methylthio)-2-[4-(methylthio)phenyl]pyrimdine-5-carboxamide;

N-(4-Ethoxyphenyl)-4-(methylamino)-6-(methylthio)-2-[4-(methylthio)phenyl]pyrimidine-5-carboxamide;

4-Chloro-N-(3,4-dimethylphenyl)-6-(methylthio)-2-[4-(methylthio) phenyl]pyrimidine-5-carboxamide;

N-(3,4-Dimethylphenyl)-6-(methylthio)-2-[4-(methylthio)phenyl]-4-piperazin -1-ylpyrimidine-5-carboxamide;

4-(Benzylamino)-N-(3,4-dimethylphenyl)-6-(methylthio)-2-[4-(methylthio)phenyl]pyrimidine-5-carboxamide;

N-(3,4-Dimethylphenyl)-4-(4-methylpiperazin-1-yl)-6-(methylthio)-2-[4-(methylthio)phenyl]pyrimidine-5-carboxamide;

2-(4-Fluorophenyl)-4-(methylamino)-6-(methylthio)-N[4-(methylthio)phenyl]pyrimidine-5-carboxamide;

N-(4-Bromophenyl)-4-[(2-hydroxyethyl)amino]-6-(methylthio)-2-pyridin-4-ylpyrimidine-5-carboxamide;

N-(4-Chlorophenyl)-4-[(2-hydroxyethylamino]-6-(methylthio)-2-pyridin-4-ylpyrimidine-5-carboxamide;

N-(3,4-Dimethylphenyl)-4-hydrazino-6-(methylthio)-2-[4-(methylthio)phenyl]pyrimidine-5-carboxamide;

N-(2,4-Dimethylphenyl)-4-[(2-hydroxyethyl)amino]-6-(methylthio)-2-pyridin-4-ylpyrimidine-5-carboxamide;

N-(3,4-Difluorophenyl)-4-[(2-hydroxyethyl)amino]-6-(methylthio)-2-[4-(methylthio)phenyl]pyrimidine-5-carboxamide;

4-[Ethyl(hydroxymethyl)amino]-N-(4-methylphenyl)-6-(methylthio)-2-pyridin-4-ylpyrimidine-5-carboxamide;

N-(3,4-Difluorophenyl)-4-(methylamino)-6-(methylthio)-2-[4-(methylthio)phenyl]pyrimidine-5-carboxamide;

2-(3-Fluorophenyl)-4-[(2-hydroxyethyl)amino]-6-(methylthio)-N-[(4-methylthio)phenyl]pyrimidine-5-carboxamide;

N-(3,4-Difluorophenyl)-2-(4-ethoxyphenyl)-4-[(2-hydroxyethyl)amino]-6-(methylthio)pyrimidine-5-carboxamide;

4-[(2-Hydroxyethyl)amino]-N-(4-methoxyphenyl)-6-(methylthio)-2-pyridin-4-ylpyrimidine-5-carboxamide;

N-(4-Fluorophenyl)-4-{[1 -(hydroxymethyl)propyl]amino}-6-(methylthio)-2-pyridin-4-ylpyrimidine-5-carboxamide;

2[4-(Dimethylamino)phenyl]-4-(methylamino)-N-(4-methoxyphenyl)-6-(methylthio)pyrimidine-5-carboxamide;

N-(3,4-Dimethylphenyl)-4-[(2-hydroxyethyl)amino]-2-(4-{[(2-hydroxyethyl)amino]sulfonyl}phenyl)-6-(methylthio)pyrimidine-5-carboxamide;

N-(4-Methoxyphenyl)-4-(methylamino)-6-(methylthio)-2-pyridin-3-ylpyrimidine-5-carboxamide orthophosphoric acid salt;

N-(4-Methoxyphenyl)-4-(methylamino)-6-(methylthio)-2-pyridin-3 -ylpyrimidine-5-carboxamide hydrochloric acid salt;

N-(4-Methoxyphenyl)-4-(methylamino)-6-(methylthio)-2-pyridin-3 -ylpyrimidine-5-carboxamide di-mesylate salt;

N-(4-Methoxyphenyl)-4-(methylamino)-6-(methylthio)-2-pyridin-3-ylpyrimidine-5-carboxamide mesylate salt;

N-(4-Methoxyphenyl)-4-(methylamino)-6-(methylthio)-2-pyridin-3-ylpyrimidine-5-carboxamide oxalate salt; and N-(4-Methoxyphenyl)-4-(methylamino)-6-(methylthio)-2-pyridin-3-ylpyrimidine-5-carboxamide bezylate salt.

3. The compound of claim 1, wherein when halogen is present, the halogen is fluorine, chlorine, bromine or iodine; when alkyl group is present, the alkyl group is methyl, ethyl, n-propyl, isopropyl or n-butyl; when haloalkyl group is present, the haloalkyl group is chloromethyl, chloroethyl, trifluoromethyl, trifluoroethyl, dichloromethyl or dichloroethyl; when aminocycloalkyl group is present, the aminocycloalkyl group is —NH—cylcopropyl, —NH-cyclopentyl or —NH-cyclohexyl; when monoalkylamino group is present, the monoalkylamino group is —NHCH$_3$, —NHC$_2$H$_5$, —NHC$_3$H$_7$ or —NHC$_6$H$_{13}$; when dialkylamino group is present, the dialkylamino group is —N(CH$_3$)$_2$, —NCH$_3$(C$_2$H$_5$) or —N(C$_2$H$_5$)$_2$; when —NH(C$_1$C$_5$)—X having linear or branched (C$_1$-C$_5$) alkyl group is present, the linear or branched (C$_1$-C$_5$) alkyl group is methyl, ethyl, n-propyl, isopropyl or n-butyl; when X is aryl group, the aryl group is phenyl or naphthyl; when heteroaryl group is present, the heteroaryl group is pyridyl, thienyl, furyl, pyrrolyl, oxazolyl, thiazolyl, imidazolyl, isooxazolyl, oxadiazolyl, triazolyl, thiadiazolyl, tetrazolyl, pyrimidinyl, benzopyranyl, benzofuranyl, benzimidazolyl, benzoxazolyl, benzothiazolyl, benzopyrrolyl, benzoxadiazolyl or benzothiadiazolyl; when heterocyclyl group is present, the heterocyclyl group is pyrrolidinyl, morpholinyl, thiomorpholinyl, piperidinyl or piperazinyl; when aminoheterocyclyl group is present, the aminoheterocyclyl group is aminopiperazinyl or aminomorpholine; when aminoalkanol is present, the aminoalkanol is —NH—(CH$_2$)$_q$OH, the methylene group may be substituted for alkyl or —OH; when alkylhydrazine is present, the alkylhydrazine is —N(CH$_3$)NH$_2$, —N(C$_2$H$_5$)NH$_2$ or —N(C$_3$H$_7$)NH$_2$; when linear or branched (C$_1$-C$_6$) alkoxy group is present, the linear or branched (C$_1$-C$_6$) alkoxy group is methoxy, ethoxy, n-propoxy or isopropoxy; when aminoalkyl group is present, the aminoalkyl group is —NHCH$_3$, —NHC$_2$H$_5$ or —NHC$_3$H$_7$; when acyl group is present, the acyl group is —C(=O)CH$_3$, —C(=O)CF$_3$, —C(=O)C$_2$H$_5$, —C(=O)C$_3$H$_7$, -C(=S)CH$_3$, —C(=S)CF$_3$, —C(=S)C$_2$H$_5$, —C(=S)C$_3$H$_7$ or benzoyl; when aminoacyl group is present, the aminoacyl group is —NHC(=O)CH$_3$, —NHC(=O)CF$_3$, -NHC(=O)C$_2$H$_5$, —NHC(=O)C$_3$H$_7$ or —NHC(=O)C$_6$H$_{13}$; when alkoxycarbonyl group is present, the alkoxycarbonyl group is methoxycarbonyl, ethoxycarbonyl, n-propoxycarbonyl or isopropoxycarbonyl; when alkoxyalkyl group is present, the alkoxyalkyl group is methoxymethyl, ethoxymethyl, methoxyethyl or ethoxyethyl; when linear or branched (C$_1$-C$_6$) alkyl group is present, the linear or branched (C$_1$-C$_6$) alkyl group is methyl, ethyl, n-propyl, isopropyl, n-butyl, isobutyl, t-butyl, n-pentyl, isopentyl or hexyl; when alkylhalide is present, the alkylhalide is —CH$_2$Cl or —CH$_2$CH$_2$Cl; when alkylester is present, the alkylester is —CH$_2$OCOC$_2$H$_5$ or —CH$_2$OCOC$_3$H$_7$; when acyihydrazide group is present, the acylhydrazide group is —NHNH(C=O)CH$_3$ or —NHNH(C=O)CF$_3$; when aminoaryl group is present, the aminoaryl group is phenyl amino or naphthyl amino; when aminoheteroaryl group is present, the aminoheteroaryl group is thienylamino, pyridylamino or pyrimidyl amino; when aryloxy group is present, the aryloxy group is phenoxy or napthoxy; and when heteroarylamino group is present, the heteroarylamino group is thienylamino, pyridylamino or pyrimidyl amino.

4. The compound of claim 1, wherein A and B are cyclic rings, substituted or unsubstituted 5 to 10 membered ring systems, that are monocyclic or bicyclic, saturated, partially saturated or aromatic, containing 1 to 4 hetero atoms selected from O, S and N.

5. A compound of formula (I)

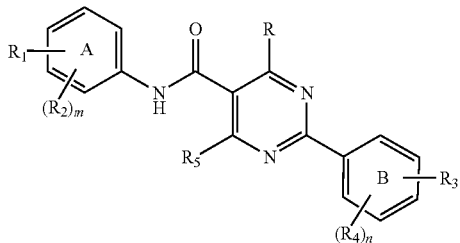

and pharmaceutically acceptable salts thereof,
wherein A is phenyl, B is pyridyl, R is —NHCH$_3$, R$_1$ and R$_3$ are hydrogen, R$_2$ is methoxy, R$_5$ is —SCH$_3$, R$_4$ is hydrogen, and m and n are 1.

6. The compound of claim 5, wherein the pharmaceutically acceptable salt is selected from the group consisting of a hydrochloride, phosphonate, mesylate, besylate, tosylate, and oxalate salt.

7. A pharmaceutical composition comprising a compound of formula (I) according to claim 1, as an active ingredient, along with a pharmaceutically acceptable carrier, diluent, excipient or solvate.

8. The pharmaceutical composition according to claim 7, wherein the pharmaceutical composition is a tablet, capsule, powder, syrup, solution, aerosol or suspension.

9. The pharmaceutical composition according to claim 7, wherein the amount of the compound of formula (I) in the composition is less than 70% by weight.

10. A method of treatment of a pain disorder in a mammal comprising administering an effective amount of a compound according to claim 1 to a mammal in need thereof.

11. A method of treatment of rheumatoid arthritis, comprising administering an effective amount of a compound according to claim 1 to a mammal in need thereof.

* * * * *